US008940534B2

(12) United States Patent
Sandig et al.

(10) Patent No.: US 8,940,534 B2
(45) Date of Patent: Jan. 27, 2015

(54) IMMORTALIZED AVIAN CELL LINES FOR VIRUS PRODUCTION

(75) Inventors: Volker Sandig, Berlin (DE); Ingo Jordan, Berlin (DE)

(73) Assignee: Probiogen AG, Berlin (DE)

( * ) Notice: Subject to any disclaimer, the term of this patent is extended or adjusted under 35 U.S.C. 154(b) by 2195 days.

(21) Appl. No.: 10/578,043

(22) PCT Filed: Nov. 3, 2004

(86) PCT No.: PCT/EP2004/052789
§ 371 (c)(1),
(2), (4) Date: Jan. 9, 2008

(87) PCT Pub. No.: WO2005/042728
PCT Pub. Date: May 12, 2005

(65) Prior Publication Data

US 2008/0227146 A1 Sep. 18, 2008

(30) Foreign Application Priority Data

Nov. 3, 2003 (EP) .................................... 03025158

(51) Int. Cl.

| | |
|---|---|
| ***C12N 5/16*** | (2006.01) |
| ***C07K 14/005*** | (2006.01) |
| ***A61K 39/12*** | (2006.01) |
| ***A61K 48/00*** | (2006.01) |
| ***C12N 5/073*** | (2010.01) |
| ***C12N 7/00*** | (2006.01) |

(52) U.S. Cl.
CPC ............... *C07K 14/005* (2013.01); *A61K 39/12* (2013.01); *A61K 48/0091* (2013.01); *C12N 5/0603* (2013.01); *C12N 7/00* (2013.01); *C12N 2710/10222* (2013.01); *C12N 2710/10252* (2013.01); *C12N 2710/10322* (2013.01); *C12N 2710/10352* (2013.01); *C12N 2710/24122* (2013.01)
USPC ........................... 435/349; 435/455; 435/467

(58) Field of Classification Search
CPC . A61K 39/12; A61K 48/0091; C07K 14/005; C12N 2710/10222; C12N 2710/10252
USPC ......................................... 435/349, 455, 467
See application file for complete search history.

(56) References Cited

U.S. PATENT DOCUMENTS

| | | | | |
|---|---|---|---|---|
| 5,672,485 | A | 9/1997 | Foster et al. | |
| 5,830,723 | A | 11/1998 | Foster et al. | |
| 5,879,924 | A | 3/1999 | Foster et al. | |
| 6,207,415 | B1 | 3/2001 | Foster et al. | |
| 6,255,108 | B1 * | 7/2001 | Bouquet et al. | 435/349 |
| 7,192,759 | B1 * | 3/2007 | Pau et al. | 435/235.1 |
| 2001/0016348 | A1 | 8/2001 | Bouquet et al. | |

FOREIGN PATENT DOCUMENTS

| | | |
|---|---|---|
| WO | WO 9700326 | 1/1997 |
| WO | WO 97/08307 | 3/1997 |
| WO | 99/09194 | 2/1999 |
| WO | 2004/015118 | 2/2004 |
| WO | 2004/022729 | 3/2004 |
| WO | 2005/007840 | 1/2005 |

OTHER PUBLICATIONS

Baghi et al., The retinoblastoma protein copurifies with E2F-I, an E1A-regulated inhibitor of the transcription factor E2F Cell vol. 65, Issue 6, Jun. 14, 1991, pp. 1063-1072.*
Renee et al., Nature 357, 82-85 (May 7, 1992); Inhibition of p53 transactivation required for transformation by adenovirus early 1B protein.*
Sarnow et al Adenovirus E1b-58kd tumor antigen and SV40 large tumor antigen are physically associated with the same 54 kd cellular protein in transformed cells Cell vol. 28, Issue 2, Feb. 1982, pp. 387-394.*
Debbas et al Wild-type p53 mediates apoptosis by E1A, which is inhibited by E1B Genes Dev. Apr. 1993;7(4):546-54.*
Fukuda et al [Cancer Research 63, 4434-4440, Aug. 1, 2003] E1A, E1B Double-restricted Adenovirus for Oncolytic Gene Therapy of Gallbladder Cancer1.*
Wikipedia, Bat adenovirus TJM last visited Mar. 12, 2014.*
Bangari et al Development of nonhuman adenoviruses as vaccine vectors, Rew Vaccine vol. 24, Issue 7, Feb. 13, 2006, pp. 849-862.*
Bennett MR, Macdonald K, Chan SW, Boyle JJ, Weissberg PL. Cooperative interactions between RB and p53 regulate cell proliferation, cell senescence, and apoptosis in human vascular smooth muscle cells from atherosclerotic plaques. Circ Res. Apr. 6, 1998;82(6):704-12.
Boyce-Jacino et al., Multiple complex families of endogenous retroviruses are highly conserved in the genus Gallus. J. Virol 66 (8): 4919-29 (1992).
Brudno, I. A. et al., “Pharaoh” line culture of Japanese quail cells as a leukosis-free system for virus reproduction. Vopr. Virusol. 97-100 (1980)—Abstract.
Brugge, J. S. , Erikson, R. L., Identification of a transformation-specific antigen induced by an avian sarcoma virus. Nature 269: 346-8 (1977).
Chiocca, S. et al., Identification of a novel antiapoptotic protein, GAM-1, encoded by the CELO adenovirus. J. Virol. 71: 3168-77 (1997).
Chiocca, S. et al., The complete DNA sequence and genomic organization of the avian adenovirus CELO. J. Virol. 70: 2939-49 (1996).

(Continued)

*Primary Examiner* — Maria Leavitt
(74) *Attorney, Agent, or Firm* — McDonnell Boehnen Hulbert & Berghoff LLP

(57) ABSTRACT

The present invention relates to immortalized avian cell lines suitable for production of biologicals or viruses for vaccination. In particular, the cell lines are derived from primary cells which are transformed with at least two viral or cellular genes, one of which causes cell cycle progression whereas the other interferes with innate protective mechanisms of the cell induced by dysregulated replication. The invention moreover relates to the production of said immortalized cell lines and their use for producing biologicals or viruses for vaccination.

17 Claims, 6 Drawing Sheets

(56) References Cited

OTHER PUBLICATIONS

Figure 1:
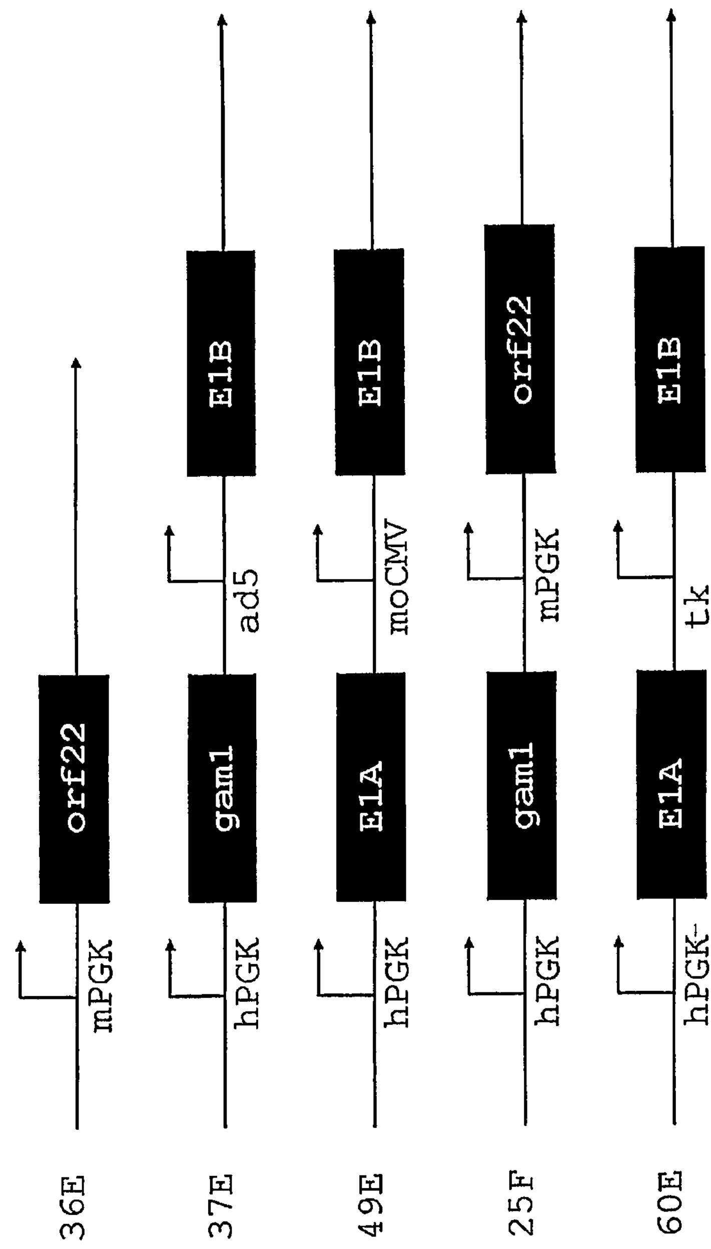

Cowen, B. S. , Braune, M. O. , The propagation of avian viruses in a continuous cell line (QT35) of Japanese quail origin. Avian Dis 32 (2): 282-97 (1988).
Crittenden et al., Host gene control of endogenous avian leukosis virus production. Virology 57 (1) : 128-38 (1974).
Curatolo et al., Culture conditions induce the appearance of immortalized C3H mouse cell lines. In Vitro 20 : 597-601 (1984).
Drexler, I. et al., Highly attenuated modified vaccinia virus Ankara replicates in baby hamster kidney cells, a potential host for virus propagation, but not in various human transformed and primary cells. J. Gen. Virol. 79 (Pt2): 347-52 (1998).
Escoffier, C., Gerlier, D., Infection of chicken embryonic fibroblasts by measles virus: adaptation at the virus entry level. J. Virol. 73: 5220-4 (1999).
Fallaux, F. J. et al., New helper cells and matched early region 1-deleted adenovirus vectors prevent generation of replication-competent adenoviruses. Hum. Gene Ther. 9 : 1909-17 (1998).
Forsyth, N. R. et al., Telomerase and differentiation in multicellular organisms: turn it off, turn it on, and turn it off again. Differentiation 69 (4-5): 188-97 (2002).
Gallegos Gallegos, R. M. et al., Rabies veterinary virus vaccine produced in BHK-21 cells grown on microcarriers in a bioreactor. Arch. Med. Res. 26: 59-63 (1995).
Givol I, Givol D, Rulong S, Resau J, Tsarfaty I, Hughes SH. Overexpression of human p21waf1/cip1 arrests the growth of chicken embryo fibroblasts transformed by individual oncogenes. Oncogene. Dec. 21, 1995;11(12):2609-18.
Graham, F. L. et al., Characteristics of a human cell line transformed by DNA from human adenovirus type 5. J. Gen. Virol. 36: 59-74 (1977).
Guilhot, C. et al., The 12S adenoviral E1A protein immortalizes avian cells and interacts with the avian RB product. Oncogene 8 : 619-24 (1993).
Gumusderelioglu M. et al., Rabies virus production in non-woven polyester fabric(NWPF) packed-bed reactors. Biotechnol. Appl. Biochem. 33: 167-72 (2001).
Hahn, W. C. et al., Creation of human tumour cells with defined genetic elements. Nature 400: 464-8 (1999).
Hartl, M. et al., Molecular targets of the oncogenic transcription factor jun. Curr. Cancer Drug Targets 3: 41-55 (2003).
Harvey, et al., p53 alteration is a common event in the spontaneous immortalization of primary BALB/c murine embryo fibroblasts. Genes and Development 5: 2375-2385 (1991).
Hussain, A. I. et al., Identification and characterization of avian retroviruses in chicken embryo-derived yellow fever vaccines: investigation of transmission to vaccine recipients. J. Virol. 77 : 1105-11 (2003).
Jha KK, Banga S, Palejwala V, Ozer HL. SV40-Mediated immortalization. Exp Cell Res. Nov. 25, 1998;245(1):1-7.
Johnson, J. A. , Heneine, W., Characterization of endogenous avian leukosis viruses in chicken embryonic fibroblast substrates used in production of measles and mumps vaccines. J. Virol. 75: 3605-12 (2001).
Kim H, You S, Kim IJ, Foster LK, Farris J, Ambady S, Ponce de León FA, Foster DN. Alterations in p53 and E2F-1 function common to immortalized chicken embryo fibroblasts. Oncogene. May 10, 2001;20(21):2671-82.
Lee, W. P. et al., Adenovirus type 5 E1A sensitizes hepatocellular carcinoma cells to gemcitabine. Cancer Res. 63: 6229-36 (2003).
Lehrmann, H. , Cotton, M. , Characterization of CELO virus proteins that modulate the pRb/E2F pathway. J. Virol. 73: 6517-25 (1999).
Li, P. et al., DNA-binding proteins of chick embryo lethal orphan virus: lack of complementation between early proteins of avian and human adenoviruses. J. Gen. Virol. 65 (Pt 10): 1817-25 (1984).
Lubiniecki, A. S. , Continuous cell substrate considerations. Bioprocess Technol. 10: 495-513 (1990).
Martin, G. S. , Rous sarcoma virus: a function required for the maintenance of the transformed state. Nature 227: 1021-3 (1970).
May, J. T. et al., A study of the sequences of chicken embryo lethal orphan (CELO) virus DNA present in a transformed hamster cell line with use of specific fragments of the virus genome. Virology 68: 483-9 (1975).
Merten, O. W. et al., Production of influenza virus in cell cultures for vaccine preparation. Adv. Exp. Med. Biol. 397: 141-51 (1996).
Munoz, N. et al., Epidemiologic classification of human papillomavirus types associated with cervical cancer. N. Engi., J. Med. 34816): 518-27 (2003).
Pasteau S, Loiseau L, Brun G. Proliferation of chicken neuroretina cells induced by v-src, in vitro, depends on activation of the E2F transcription factor. Oncogene. Jul. 3, 1997;15(1):17-28.
Pau, M. G. et al., The human cell line PER.C6 provides a new manufacturing system for the production of influenza vaccines. Vaccine 19: 2716-21 (2001).
Pay, T. W. et al., Production of rabies vaccine by an industrial scale BHK 21 suspension cell culture process. Dev. Biol. Stand 60: 171-4 (1985).
Pereira-Smith, Hybrids from fusion of normal human T lymphocytes with immortal human cells exhibit limited life span. J. Cell Physio. 144: 546-9 (1990).
Putzer, B. M. et al., E1A is sufficient by itself to induce apoptosis independent of p53 and other adenoviral gene products. Cell Death Differ. 7: 177-88 (2000).
Rocchi, G., Salvadori, A. Experience with vaccination with attenuated rubella vaccine (strain HPV-77 adapted to duck cells, 5th passage) Nuovi Ann. Ig Microbiol. 21: 336-40 (1970).
Ronfort, C. et a)., Defective retroviral endogenous RNA is efficiently transmitted by infectious particles produced on an avian retroviral vector packaging cell line. Virology 207: 271-5 (1995).
Shahabuddin, M. et al., No evidence of infectious retroviruses in measles virus vaccines produced in chicken embryo cell cultures. Clin. Microbiol. 39: 675-84 (2001).
Shaw et al. Preferential transformation of human neuronal cells by human adenoviruses and the origin of HEK 293 cells. Faseb J 16 (8): 869-71 (2002).
Smith et al., Replicative senescence: implications for in vivo aging and tumor suppression. Science 273: 63-67 (1996).
Smith, L. M. et al., Novel endogenous retroviral sequences in the chicken genome closely related to HPRS-103 (subgroup J) avian leukosis virus. J. Gen. Virol. 80 (ptl) : 261-8 (1999).
Tree, J. A. et al., Comparison of large-scale mammalian cell culture systems with egg culture for the production of influenza virus A vaccine strains. Vaccine 19 : 3444-50 (2001).
Tsang, S. X. et al., Evidence of avian leukosis virus subgroup E and endogenous avian virus in measles and mumps vaccines derived from chicken cells: investigation of transmission to vaccine recipients. J. Virol. 73: 5843-51 (1999).
Ulrich E, Boehmelt G, Bird A, Beug H. Immortalization of conditionally transformed chicken cells: loss of normal p53 expression is an early step that is independent of cell transformation. Genes Dev. May 1992;6(5):876-87.
Wazer De, Liu XL, Chu Q, Gao Q, Band V. Immortalization of distinct human mammary epithelial cell types by human papilloma virus 16 E6 or E7. Proc Natl Acad Sci U S A. Apr. 25, 1995;92(9):3687-91.
Weekly Epidemiological Record of the WHO (73) 28 (1998).
Williams BO, Remington L, Albert DM, Mukai S, Bronson RT, Jacks T. Cooperative tumorigenic effects of germline mutations in Rb and p53. Nat Genet. Aug. 1994;7(4):480-4.
Witter, R. L., Induction of strong protection by vaccination with partially attenuated serotype 1 Marek's disease viruses. Avian Dis. 46: 925-37 (2002).
Guilhot, et al., "The 12S adenoviral E1A protein immortalizes avian cells and interacts with the avian RB product", vol. 8, No. 3, pp. 619-624, (1993).
Ko, et al. "p53: puzzle and paradigm", vol. 10, No. 9, pp. 1054-1072, (1996).
Van Den Elsen, et al., "The relationship between region E1a and E1b of human adenoviruses in cell transformation", vol. 18, No. 2, pp. 175-185, (1982).

(56) References Cited

OTHER PUBLICATIONS

White, et al., "Role of Adenovirus E1B Proteins in Transformation: Altered Organization of Intermediate Filaments in Transformed Cells That Express the 19-Kilodalton Protein", vol. 10, No. 1, pp. 120-130, (1990).
Blanchard et al., "Modified vaccinia virus Ankara undergoes limited replication in human cells and lacks several immunomodulatory proteins: implications for use as a human vaccine." Journal of General Virology 79(Pt5):1159-67 (1998).
Bossart et al., "Membrane fusion tropism and heterotypic functional activities of the Nipah virus and Hendra virus envelope glycoproteins." Journal of Virology 76(22):11186-98 (2002).
Butel, "Viral carcinogenesis: revelation of molecular mechanisms and etiology of human disease." Carcinogenesis 21 (3):405-26 (2000).
Carroll and Moss, "Host range and cytopathogenicity of the highly attenuated MVA strain of vaccinia virus: propagation and generation of recombinant viruses in a nonhuman mammalian cell line." Virology 238(2): 198-211 (1997).
Chellappan et al., "Adenovirus E1A, simian virus 40 tumor antigen, and human papillomavirus E7 protein share the capacity to disrupt the interaction between transcription factor E2F and the retinoblastoma gene product." Proc. Natl. Acad. Sci. U.S.A. 89(10):4549-53 (1992).
Crucell R&D Partners & Licensees list updated Nov. 22, 2010, pp. 1-4, printed Jan. 12, 2010.
Hawley-Nelson et al., "HPV16 E6 and E7 proteins cooperate to immortalize human foreskin keratinocytes." EMBO J. 8(12):3905-10 (1989).
Herniou et al., "Retroviral Diversity and Distribution in Vertebrates." Journal of Virology, 72(7):5955-66 (1998).
Huang et al., "The duck genome and transcriptome provide insight into an avian influenza virus reservoir species." Nature Genetics 45:776-83 (2013).
Huang et al., Supplement to "The duck genome and transcriptome provide insight into an avian influenza virus reservoir species." Nature Genetics, pp. 1-63 (2013).
Ivanov et al., "Establishment of a duck embryo permanent cell culture." Experimental pathology and parasitology, Jan. 1998, pp. 67-71 (1998).
Ivanov et al., "P[r]opagation of avian virus strains in the permanent duck embryo cell line DEC 99." Experimental pathology and parasitology, Apr. 5, 2001, pp. 31-34 (2001).
Jiang and Milner, "Bcl-2 constitutively suppresses p53-dependent apoptosis in colorectal cancer cells." Genes and Development 17(7):832-37 (2003).
Kang and Shadduck, "Establishment of duck cell line derived from experimental tumor induced by 20-methylcholanthrene." In Vitro 13(12):849-56 (1977).
Kim et al., "Structural basis for the inactivation of retinoblastoma tumor suppressor by SV40 large T antigen." EMBO 20(1&2):295-304 (2001).
Majid, Declaration by Mehtali Majid of Dec. 8, 2010, pp. 1-3 (2010).
Marcovici et al., ATCC® catalogue extract for ATCC® Cell Deposit CCL-141™ pp. 1-2, printed Jan. 12, 2010.
Martin and Berk, "Adenovirus E1B 55K represses p53 activation in vitro." Journal of Virology 72(4):3146-54 (1998).
Moss et al. "Host range restricted, non-replicating vaccinia virus vectors as vaccine candidates." Adv Exp Med Biol 397:7-13 (1996).
Olu et al. Transcription of anti-apoptotic proteins from CELO and EDS avian adenoviruses at early stages of infection: Mol Gen Milrobiol Virusol 4:15-17 (2000). English Abstract submitted.
Rao et al., "The adenovirus E1A proteins induce apoptosis, which is inhibited by the E1B 19-kDa and Bcl-2 proteins." Proc. Natl. Sci. U.S.A. 89(16):7742-46 (1992).
Sears and Nevins, "Signaling networks that link cell proliferation and cell fate." Journal of Biological Chemistry 277 (14):11617-20 (2002).
Shoyab and Baluda, "Homology between avian oncornavirus RNAs and DNA from several avian species." Journal of Virology 16(6):1492-1502 (1975).
Sutter and Moss, "Nonreplicating vaccinia vector efficiently expresses recombinant genes." Proc. Natl. Sci. U.S.A. 89(22):10847-51 (1992).
Thomas et al., "Early region 1 transforming functions are dispensable for mammary tumorigenesis by human adenovirus type 9." Journal of Virology 73:3071-79 (1999).
Thomas et al., "p53 mediates bcl-2 phosphorylation and apoptosis via activation of the Cdc42/JNK1 pathway." Oncogene 19(46):5259-69 (2000).
Wikipedia, "Cell culture" pp. 1-10, printed Mar. 31, 2009.
World Health Organization, WHO No. 28, "Reverse transcriptase activity in chicken-cell derived vaccine," 73:209-26 (1998).

* cited by examiner

B

A

Fig. 2

SEQUENCE LISTING

```
<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer
      VS182

<400> SEQUENCE: 1

actcgagctg acgtgtagtg tatt                                         24


<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer
      VS183

<400> SEQUENCE: 2

cacacgcaat cacaggtt                                                18


<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer
      VS184

<400> SEQUENCE: 3

actcgagtca tggaggcttg ggagt                                        25


<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer
      VS185

<400> SEQUENCE: 4

acacatttca gtacctca                                                18
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer VintSA-F

<400> SEQUENCE: 5
aaggtaccct ccctagtccc agtga 25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer Vint SA-R

<400> SEQUENCE: 6
caatgtacag agtgggctcc tgtgg 25

<210> SEQ ID NO 7
<211> LENGTH: 6471
<212> TYPE: DNA
<213> ORGANISM: Artificial Sequence
<220> FEATURE:
<223> OTHER INFORMATION: Description of Artificial Sequence: Plasmid pEFAd5E1A

<400> SEQUENCE: 7
gtaccgaatt caagcttcgt gaggctccgg tgcccgtcag tgggcagagc gcacatcgcc 60
cacagtcccc gagaagttgg ggggaggggt cggcaattga accggtgcct agagaaggtg 120
gcgcggggta aactgggaaa gtgatgtcgt gtactggctc cgcctttttc ccgagggtgg 180
gggagaaccg tatataagtg cagtagtcgc cgtgaacgtt ctttttcgca acgggtttgc 240
cgccagaaca caggtaagtg ccgtgtgtgg ttcccgcggg cctggcctct ttacgggtta 300
tggcccttgc gtgccttgaa ttacttccac ctggctccag tacgtgattc ttgatcccga 360
gctggagcca ggggcgggcc ttgcgcttta ggagcccctt cgcctcgtgc ttgagttgag 420
gcctggcctg ggcgctgggg ccgccgcgtg cgaatctggt ggcaccttcg cgcctgtctc 480
gctgctttcg ataagtctct agccatttaa aatttttgat gacctgctgc gacgcttttt 540
ttctggcaag atagtcttgt aaatgcgggc caggatctgc acactggtat ttcggttttt 600
gggcccgcgg ccggcgacgg ggcccgtgcg tcccagcgca catgttcggc gaggcggggc 660
ctgcgagcgc ggccaccgag aatcggacgg gggtagtctc aagctggccg gcctgctctg 720
gtgcctggcc tcgcgccgcc gtgtatcgcc ccgccctggg cggcaaggct ggcccggtcg 780
gcaccagttg cgtgagcgga aagatggccg cttcccggcc ctgctccagg gggctcaaaa 840
tggaggacgc ggcgctcggg agagcgggcg ggtgagtcac ccacacaaag gaaaagggcc 900
tttccgtcct cagccgtcgc ttcatgtgac tccacggagt accgggcgcc gtccaggcac 960
ctcgattagt tctggagctt ttggagtacg tcgtctttag gttgggggga ggggttttat 1020
gcgatggagt ttccccacac tgagtgggtg gagactgaag ttaggccagc ttggcacttg 1080
atgtaattct ccttggaatt tggccttttt gagtttggat cttggttcat tctcaagcct 1140
cagacagtgg ttcaaagttt ttttcttcca tttcaggtgt cgtgaacact cgagctgacg 1200
tgtagtgtat ttatacccgg tgagttcctc aagaggccac tcttgagtgc cagcgagtag 1260
agttttctcc tccgagccgc tccgacaccg ggactgaaaa tgagacatat tatctgccac 1320

-continued

```
ggaggtgtta ttaccgaaga aatggccgcc agtcttttgg accagctgat cgaagaggta   1380
ctggctgata atcttccacc tcctagccat tttgaaccac ctacccttca cgaactgtat   1440
gatttagacg tgacggcccc cgaagatccc aacgaggagg cggtttcgca gatttttccc   1500
gactctgtaa tgttggcggt gcaggaaggg attgacttac tcacttttcc gccggcgccc   1560
ggttctccgg agccgcctca cctttcccgg cagcccgagc agccggagca gagagccttg   1620
ggtccggttt ctatgccaaa ccttgtaccg gaggtgatcg atcttacctg ccacgaggct   1680
ggctttccac ccagtgacga cgaggatgaa gagggtgagg agtttgtgtt agattatgtg   1740
gagcaccccg ggcacggttg caggtcttgt cattatcacc ggaggaatac gggggaccca   1800
gatattatgt gttcgctttg ctatatgagg acctgtggca tgtttgtcta cagtaagtga   1860
aaattatggg cagtgggtga tagagtggtg ggtttggtgt ggtaattttt tttttaattt   1920
ttacagtttt gtggtttaaa gaattttgta ttgtgatttt tttaaaaggt cctgtgtctg   1980
aacctgagcc tgagcccgag ccagaaccgg agcctgcaag acctacccgc cgtcctaaaa   2040
tggcgcctgc tatcctgaga cgcccgacat cacctgtgtc tagagaatgc aatagtagta   2100
cggatagctg tgactccggt ccttctaaca cacctcctga gatacacccg gtggtcccgc   2160
tgtgccccat taaaccagtt gccgtgagag ttggtgggcg tcgccaggct gtggaatgta   2220
tcgaggactt gcttaacgag cctgggcaac ctttggactt gagctgtaaa cgccccaggc   2280
cataaggtgt aaacctgtga ttgcgtgtgg aattctagaa gctcgctgat cagcctcgac   2340
tgtgccttct agttgccagc catctgttgt ttgcccctcc cccgtgcctt ccttgaccct   2400
ggaaggtgcc actcccactg tcctttccta ataaaatgag gaaattgcat cgcattgtct   2460
gagtaggtgt cattctattc tggggggtgg ggtggggcag gacagcaagg gggaggattg   2520
ggaagacaat agcaggcatg ctggggatgg cccgggctct atggcttctg aggcggaaag   2580
aaccagctgg ggctctaggg ggtatcccca cgcgccctgt agcggcgcat taagcgcggc   2640
gggtgtggtg gttacgcgca gcgtgaccgc tacacttgcc agcgccctag cgcccgctcc   2700
tttcgctttc ttcccttcct ttctcgccac gttcgccggc tttccccgtc aagctctaaa   2760
tcggggcatc cctttagggt tccgatttag tgctttacgg cacctcgacc ccaaaaaact   2820
tgattagggt gatggttcac gtagtgggcc atcgccctga tagacggttt ttcgcccttt   2880
gacgttggag tccacgttct ttaatagtgg actcttgttc caaactggaa caacactcaa   2940
ccctatctcg gtctattctt ttgatttata agggattttg gggatttcgg cctattggtt   3000
aaaaaatgag ctgatttaac aaaaatttaa cgcgaattaa ttctgtggaa tgtgtgtcag   3060
ttagggtgtg gaaagtcccc aggctcccca ggcaggcaga agtatgcaaa gcatgcatct   3120
caattagtca gcaaccaggt gtggaaagtc cccaggctcc ccagcaggca gaagtatgca   3180
aagcatgcat ctcaattagt cagcaaccat agtcccgccc ctaactccgc ccatcccgcc   3240
cctaactccg cccagttccg cccattctcc gccccatggc tgactaattt tttttattta   3300
tgcagaggcc gaggccgcct ctgcctctga gctattccag aagtagtgag gaggcttttt   3360
tggaggccta ggcttttgca aaaagctccc gggaggtcca caatgattga acaagatgga   3420
ttgcacgcag gttctccggc cgcttgggtg gagaggctat tcggctatga ctgggcacaa   3480
cagacaatcg gctgctctga tgccgccgtg ttccggctgt cagcgcaggg gcgcccggtt   3540
ctttttgtca agaccgacct gtccggtgcc ctgaatgaac tccaggacga ggcagcgcgg   3600
ctatcgtggc tggccacgac gggcgttcct tgcgcagctg tgctcgacgt tgtcactgaa   3660
gcgggaaggg actggctgct attgggcgaa gtgccggggc aggatctcct gtcatctcac   3720
```

-continued

```
cttgctcctg ccgagaaagt atccatcatg gctgatgcaa tgcggcggct gcatacgctt   3780
gatccggcta cctgcccatt cgaccaccaa gcgaaacatc gcatcgagcg agcacgtact   3840
cggatggaag ccggtcttgt cgatcaggat gatctggacg aagagcatca ggggctcgcg   3900
ccagccgaac tgttcgccag gctcaaggcg cgtatgcccg acggcgagga tctcgtcgtg   3960
actcatggcg atgcctgctt gccgaatatc atggtggaaa atggccgctt ttctggattc   4020
atcgactgtg gccggctggg tgtggcggac cgctatcagg acatagcgtt ggctacccgt   4080
gatattgctg aagagcttgg cggcgaatgg gctgaccgct tcctcgtgct ttacggtatc   4140
gccgctcccg attcgcagcg catcgccttc tatcgccttc ttgacgagtt cttctgagcg   4200
ggactctggg gttcgaaatg accgaccaag cgacgcccaa cctgccatca cgagatttcg   4260
attccaccgc cgccttctat gaaaggttgg gcttcggaat cgttttccgg gacgccggct   4320
ggatgatcct ccagcgcggg gatctcatgc tggagttctt cgcccacccc aacttgttta   4380
ttgcagctta taatggttac aaataaagca atagcatcac aaatttcaca aataaagcat   4440
tttttcact gcattctagt tgtggtttgt ccaaactcat caatgtatct tatcatgtct   4500
gtataccgga tctttccgct tcctcgctca ctgactcgct gcgctcggtc gttcggctgc   4560
ggcgagcggt atcagctcac tcaaaggcgg taatacggtt atccacagaa tcaggggata   4620
acgcaggaaa gaacatgtga gcaaaaggcc agcaaaaggc caggaaccgt aaaaaggccg   4680
cgttgctggc gtttttccat aggctccgcc cccctgacga gcatcacaaa aatcgacgct   4740
caagtcagag gtggcgaaac ccgacaggac tataaagata ccaggcgttt ccccctggaa   4800
gctccctcgt gcgctctcct gttccgaccc tgccgcttac cggatacctg tccgcctttc   4860
tcccttcggg aagcgtggcg ctttctcaat gctcacgctg taggtatctc agttcggtgt   4920
aggtcgttcg ctccaagctg ggctgtgtgc acgaaccccc cgttcagccc gaccgctgcg   4980
ccttatccgg taactatcgt cttgagtcca acccggtaag acacgactta tcgccactgg   5040
cagcagccac tggtaacagg attagcagag cgaggtatgt aggcggtgct acagagttct   5100
tgaagtggtg gcctaactac ggctacacta gaaggacagt atttggtatc tgcgctctgc   5160
tgaagccagt taccttcgga aaaagagttg gtagctcttg atccggcaaa caaaccaccg   5220
ctggtagcgg tggttttttt gtttgcaagc agcagattac gcgcagaaaa aaaggatctc   5280
aagaagatcc tttgatcttt tctacggggt ctgacgctca gtggaacgaa aactcacgtt   5340
aagggatttt ggtcatgaga ttatcaaaaa ggatcttcac ctagatcctt ttaaattaaa   5400
aatgaagttt taaatcaatc taaagtatat atgagtaaac ttggtctgac agttaccaat   5460
gcttaatcag tgaggcacct atctcagcga tctgtctatt tcgttcatcc atagttgcct   5520
gactccccgt cgtgtagata actacgatac gggagggctt accatctggc cccagtgctg   5580
caatgatacc gcgagaccca cgctcaccgg ctccagattt atcagcaata aaccagccag   5640
ccggaagggc cgagcgcaga agtggtcctg caactttatc cgcctccatc cagtctatta   5700
attgttgccg ggaagctaga gtaagtagtt cgccagttaa tagtttgcgc aacgttgttg   5760
ccattgctac aggcatcgtg gtgtcacgct cgtcgtttgg tatggcttca ttcagctccg   5820
gttcccaacg atcaaggcga gttacatgat cccccatgtt gtgcaaaaaa gcggttagct   5880
ccttcggtcc tccgatcgtt gtcagaagta agttggccgc agtgttatca ctcatggtta   5940
tggcagcact gcataattct cttactgtca tgccatccgt aagatgcttt tctgtgactg   6000
gtgagtactc aaccaagtca ttctgagaat agtgtatgcg gcgaccgagt tgctcttgcc   6060
cggcgtcaat acgggataat accgcgccac atagcagaac tttaaaagtg ctcatcattg   6120
```

```
gaaaacgttc ttcggggcga aaactctcaa ggatcttacc gctgttgaga tccagttcga   6180

tgtaacccac tcgtgcaccc aactgatctt cagcatcttt tactttcacc agcgtttctg   6240

ggtgagcaaa aacaggaagg caaaatgccg caaaaaaggg aataagggcg acacggaaat   6300

gttgaatact catactcttc ctttttcaat attattgaag catttatcag ggttattgtc   6360

tcatgagcgg atacatattt gaatgtattt agaaaaataa acaaataggg gttccgcgca   6420

catttccccg aaaagtgcca cctgacgtca gatcgacgga tcgggagatc g            6471
```

```
<210> SEQ ID NO 8
<211> LENGTH: 6629
<212> TYPE: DNA
<213> ORGANISM: Artificial Sequence
<220> FEATURE:
<223> OTHER INFORMATION: Description of Artificial Sequence: Plasmid
      pEFAd5E1BSA

<400> SEQUENCE: 8

tcttccgctt cctcgctcac tgactcgctg cgctcggtcg ttcggctgcg gcgagcggta     60

tcagctcact caaaggcggt aatacggtta tccacagaat caggggataa cgcaggaaag    120

aacatgtgag caaaaggcca gcaaaagccc aggaaccgta aaaaggccgc gttgctggcg    180

tttttccata ggctccgccc ccctgacgag catcacaaaa atcgacgctc aagtcagagg    240

tggcgaaacc cgacaggact ataaagatac caggcgtttc cccctggaag ctccctcgtg    300

cgctctcctg ttccgaccct gccgcttacc ggatacctgt ccgcctttct cccttcggga    360

agcgtggcgc tttctcatag ctcacgctgt aggtatctca gttcggtgta ggtcgttcgc    420

tccaagctgg gctgtgtgca cgaacccccc gttcagcccg accgctgcgc cttatccggt    480

aactatcgtc ttgagtccaa cccggtaaga cacgacttat cgccactggc agcagccact    540

ggtaacagga ttagcagagc gaggtatgta ggcggtgcta cagagttctt gaagtggtgg    600

cctaactacg gctacactag aaggacagta tttggtatct gcgctctgct gaagccagtt    660

accttcggaa aaagagttgg tagctcttga tccggcaaac aaaccaccgc tggtagcggt    720

ggtttttttg tttgcaagca gcagattacg cgcagaaaaa aaggatctca agaagatcct    780

ttgatctttt ctacggggtc tgacgctcag tggaacgaaa actcacgtta agggattttg    840

gtcatgagat tatcaaaaag gatcttcacc tagatccttt taaattaaaa atgaagtttt    900

aaatcaatct aaagtatata tgagtaaact tggtctgaca gttaccaatg cttaatcagt    960

gaggcaccta tctcagcgat ctgtctattt cgttcatcca tagttgcctg actccccgtc   1020

gtgtagataa ctacgatacg ggagggctta ccatctggcc ccagtgctgc aatgataccg   1080

cgagacccac gctcaccggc tccagattta tcagcaataa accagccagc cggaagggcc   1140

gagcgcagaa gtggtcctgc aactttatcc gcctccatcc agtctattaa ttgttgccgg   1200

gaagctagag taagtagttc gccagttaat agtttgcgca acgttgttgc cattgctaca   1260

ggcatcgtgg tgtcacgctc gtcgtttggt atggcttcat tcagctccgg ttcccaacga   1320

tcaaggcgag ttacatgatc ccccatgttg tgcaaaaaag cggttagctc cttcggtcct   1380

ccgatcgttg tcagaagtaa gttggccgca gtgttatcac tcatggttat ggcagcactg   1440

cataattctc ttactgtcat gccatccgta agatgctttt ctgtgactgg tgagtactca   1500

accaagtcat tctgagaata gtgtatgcgg cgaccgagtt gctcttgccc ggcgtcaata   1560

cgggataata ccgcgccaca tagcagaact ttaaaagtgc tcatcattgg aaaacgttct   1620

tcggggcgaa aactctcaag gatcttaccg ctgttgagat ccagttcgat gtaacccact   1680
```

```
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgtatgcgg tgtgaaatac cgcacagatg cgtaaggaga aaataccgca   1980
tcaggaaatt gtaagcgtta ataattcaga agaactcgtc aagaaggcga tagaaggcga   2040
tgcgctgcga atcgggagcg gcgataccgt aaagcacgag gaagcggtca gcccattcgc   2100
cgccaagctc ttcagcaata tcacgggtag ccaacgctat gtcctgatag cggtccgcca   2160
cacccagccg gccacagtcg atgaatccag aaaagcggcc attttccacc atgatattcg   2220
gcaagcaggc atcgccatgg gtcacgacga gatcctcgcc gtcgggcatg ctcgccttga   2280
gcctggcgaa cagttcggct ggcgcgagcc cctgatgctc ttcgtccaga tcatcctgat   2340
cgacaagacc ggcttccatc cgagtacgtg ctcgctcgat gcgatgtttc gcttggtggt   2400
cgaatgggca ggtagccgga tcaagcgtat gcagccgccg cattgcatca gccatgatgg   2460
atactttctc ggcaggagca aggtgagatg acaggagatc ctgccccggc acttcgccca   2520
atagcagcca gtcccttccc gcttcagtga caacgtcgag cacagctgcg caaggaacgc   2580
ccgtcgtggc cagccacgat agccgcgctg cctcgtcttg cagttcattc agggcaccgg   2640
acaggtcggt cttgacaaaa agaaccgggc gcccctgcgc tgacagccgg aacacggcgg   2700
catcagagca gccgattgtc tgttgtgccc agtcatagcc gaatagcctc tccacccaag   2760
cggccggaga acctgcgtgc aatccatctt gttcaatcat gcgaaacgat cctcatcctg   2820
tctcttgatc agagcttgat cccctgcgcc atcagatcct tggcggcgag aaagccatcc   2880
agtttacttt gcagggcttc ccaaccttac cagagggcgc cccagctggc aattccggtt   2940
cgcttgctgt ccataaaacc gcccagtcta gctatcgcca tgtaagccca ctgcaagcta   3000
cctgctttct ctttgcgctt gcgttttccc ttgtccagat agcccagtag ctgacattca   3060
tccggggtca gcaccgtttc tgcggactgg ctttctacgt gaaaaggatc taggtgaaga   3120
tcctttttga taatctcatg cctgacattt atattcccca gaacatcagg ttaatggcgt   3180
ttttgatgtc attttcgcgg tggctgagat cagccacttc ttccccgata acggagaccg   3240
gcacactggc catatcggtg gtcatcatgc gccagctttc atccccgata tgcaccaccg   3300
ggtaaagttc acgggagact ttatctgaca gcagacgtgc actggccagg gggatcacca   3360
tccgtcgccc cggcgtgtca ataatatcac tctgtacatc cacaaacaga cgataacggc   3420
tctctctttt ataggtgtaa accttaaact gccgtacgta taggctgcgc aactgttggg   3480
aagggcgatc ggtgcgggcc tcttcgctat tacgccagct ggcgaaaggg ggatgtgctg   3540
caaggcgatt aagttgggta acgccagggt tttcccagtc acgacgttgt aaaacgacgg   3600
ccagtgaatt gtaatacgac tcactatagg gcgaattgaa tttagcggcc gcgaattcta   3660
ccgggtaggg gaggcgcttt tcccaaggca gtctggagca tgcgctttag cagccccgct   3720
ggcacttggc gctacacaag tggcctctgg cctcgcacac attccacatc caccggtagg   3780
cgccaaccgg ctccgttctt tggtggcccc ttcgcgccac cttctactcc tcccctagtc   3840
aggaagttcc cccccgcccc gcagctcgcg tcgtgcagga cgtgacaaat ggaagtagca   3900
cgtctcacta gtctcgtgca gatggacagc accgctgagc aatggaagcg ggtaggcctt   3960
tggggcagcg gccaatagca gctttgctcc ttcgctttct gggctcagag gctgggaagg   4020
ggtgggtccg gggcgggct caggggcggg ctcaggggcg gggcgggcgc ccgaaggtcc   4080
```

-continued

```
tccggaggcc cggcattctc gcacgcttca aaagcgcacg tctgccgcgc tgttctcctc   4140

ttcctcatct ccgggccttt ctcgagcatg gaggcttggg agtgtttgga agatttttct   4200

gctgtgcgta acttgctgga acagagctct aacagtacct cttggttttg gaggtttctg   4260

tggggctcat cccaggcaaa gttagtctgc agaattaagg aggattacaa gtgggaattt   4320

gaagagcttt tgaaatcctg tggtgagctg tttgattctt tgaatctggg tcaccaggcg   4380

cttttccaag agaaggtcat caagactttg gatttttcca caccggggcg cgctgcggct   4440

gctgttgctt ttttgagttt tataaaggat aaatggagcg aagaaaccca tctgagcggg   4500

gggtacctgc tggatttttct ggccatgcat ctgtggagag cggttgtgag acacaagaat   4560

cgcctgctac tgttgtcttc cgtccgcccg gcgataatac cgacggagga gcagcagcag   4620

cagcaggagg aagccaggcg gcggcggcag gagcagagcc catggaaccc gagagccggc   4680

ctggaccctc gggaatgaat gttgtacagg tggctgaact gtatccagaa ctgagacgca   4740

ttttgacaat tacagaggat gggcaggggc taaagggggt aaagagggag cgggggggctt   4800

gtgaggctac agaggaggct aggaatctag cttttagctt aatgaccaga caccgtcctg   4860

agtgtattac ttttcaacag atcaaggata attgcgctaa tgagcttgat ctgctggcgc   4920

agaagtattc catagagcag ctgaccactt actggctgca gccaggggat gatttgagg   4980

aggctattag ggtatatgca aaggtggcac ttaggccaga ttgcaagtac aagatcagca   5040

aacttgtaaa tatcaggaat tgttgctaca tttctgggaa cggggccgag gtggagatag   5100

atacggagga tagggtggcc tttagatgta gcatgataaa tatgtggccg gggtgcttg   5160

gcatggacgg ggtggttatt atgaatgtaa ggtttactgg ccccaatttt agcggtacgg   5220

ttttcctggc caataccaac cttatcctac acggtgtaag cttctatggg tttaacaata   5280

cctgtgtgga agcctggacc gatgtaaggg ttcggggctg tgccttttac tgctgctgga   5340

agggggtggt gtgtcgcccc aaaagcaggg cttcaattaa gaaatgcctc tttgaaaggt   5400

gtaccttggg tatcctgtct gagggtaact ccagggtgcg ccacaatgtg gcctccgact   5460

gtggttgctt catgctagtg aaaagcgtgg ctgtgattaa gcataacatg gtatgtggca   5520

actgcgagga cagggcctct cagatgctga cctgctcgga cggcaactgt cacctgctga   5580

agaccattca cgtagccagc cactctcgca aggcctggcc agtgtttgag cataacatac   5640

tgacccgctg ttccttgcat ttgggtaaca ggagggggggt gttcctacct taccaatgca   5700

atttgagtca cactaagata ttgcttgagc ccgagagcat gtccaaggtg aacctgaacg   5760

gggtgtttga catgaccatg aagatctgga aggtgctgag gtacgatgag acccgcacca   5820

ggtgcagacc ctgcgagtgt ggcggtaaac atattaggaa ccagcctgtg atgctggatg   5880

tgaccgagga gctgaggccc gatcacttgg tgctggcctg cacccgcgct gagtttggct   5940

ctagcgatga agatacagat tgaggtactg aaatggctag cagtgtaccc tccctagtcc   6000

cagtgatgag aaagagattg agtccagtcc agggagatct catccacttc tgtgttctct   6060

ccacaggagc ccactctgta caagtaaagc ggccgcgact ctagatcata atcagccata   6120

ccacatttgt agaggtttta cttgctttaa aaaacctccc acacctcccc ctgaacctga   6180

aacataaaat gaatgcaatt gttgttgtta acttgtttat tgcagcttat aatggttaca   6240

aataaagcaa tagcatcaca aatttcacaa ataaagcatt tttttcactg cattctagtt   6300

gtggtttgtc caaactcatc aatgtatctt aagattaagg gcgaattcgt ttaaacctgc   6360

aggactagtc cctttagtga gggttaattc tgagcttggc gtaatcatgg tcatagctgt   6420

ttcctgtgtg aaattgttat ccgctcacaa ttccacacaa catacgagcc ggaagcataa   6480
```

agtgtaaagc ctggggtgcc taatgagtga gctaactcac attaattgcg ttgcgctcac 6540
tgcccgcttt ccagtcggga aacctgtcgt gccagctgca ttaatgaatc ggccaacgcg 6600
cggggagagg cggtttgcgt attgggcgc 6629

<210> SEQ ID NO 9
<211> LENGTH: 8297
<212> TYPE: DNA
<213> ORGANISM: Artificial Sequence
<220> FEATURE:
<223> OTHER INFORMATION: Description of Artificial Sequence: Plasmid 49E

<400> SEQUENCE: 9
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gccaagctca 240
gaattaaccc tcactaaagg gactagtcct gcaggtttaa acgaattcgc ccttaatctt 300
aagctgccgc cccgacgttg gctgcgagcc ctgggccttc acccgaactt gggggggtggg 360 gtggggaaaa ggaagaaacg cgggcgtatt ggccccaatg gggtctcggt ggggtatcga 420
cagagtgcca gccctgggac cgaaccccgc gtttatgaac aaacgaccca acaccgtgcg 480
ttttattctg tctttttatt gccgtcatag cgcgggttcc ttccggtatt gtctccttcc 540
gtgttatcct caatctgtat cttcatcgct agagccaaac tcagcgcggg tgcaggccag 600
caccaagtga tcgggcctca gctcctcggt cacatccagc atcacaggct ggttcctaat 660
atgtttaccg ccacactcgc agggtctgca cctggtgcgg gtctcatcgt acctcagcac 720
cttccagatc ttcatggtca tgtcaaacac cccgttcagg ttcaccttgg acatgctctc 780
gggctcaagc aatatcttag tgtgactcaa attgcattgg taaggtagga acaccccccct 840 cctgttaccc aaatgcaagg aacagcgggt cagtatgtta tgctcaaaca ctggccaggc 900
cttgcgagag tggctggcta cgtgaatggt cttcagcagg tgacagttgc cgtccgagca 960
ggtcagcatc tgagaggccc tgtcctcgca gttgccacat accatgttat gcttaatcac 1020
agccacgctt ttcactagca tgaagcaacc acagtcggag gccacattgt ggcgcaccct 1080
ggagttaccc tcagacagga tacccaaggt acacctttca aagaggcatt tcttaattga 1140
agccctgctt ttggggcgac acaccacccc cttccagcag cagtaaaagg cacagccccg 1200
aacccttaca tcggtccagg cttccacaca ggtattgtta aacccataga agcttacacc 1260
gtgtaggata aggttggtat tggccaggaa aaccgtaccg ctaaaattgg ggccagtaaa 1320
ccttacattc ataataacca ccccgtccat gccaagcacc cccggccaca tatttatcat 1380
gctacatcta aaggccaccc tatcctccgt atctatctcc acctcggccc cgttcccaga 1440
aatgtagcaa caattcctga tatttacaag tttgctgatc ttgtacttgc aatctggcct 1500
aagtgccacc tttgcatata ccctaatagc ctcctcaaaa tcatcccctg gctgcagcca 1560
gtaagtggtc agctgctcta tggaatactt ctgcgccagc agatcaagct cattagcgca 1620
attatccttg atctgttgaa aagtaataca ctcaggacgg tgtctggtca ttaagctaaa 1680
agctagattc ctagcctcct ctgtagcctc acaagccccc cgctccctct ttaccccctt 1740
tagcccctgc ccatcctctg taattgtcaa aatgcgtctc agttctggat acagttcagc 1800
cacctgtaca acattcattc ccgagggtcc aggccggctc tcgggttcca tgggctctgc 1860
tcctgccgcc gccgcctggc ttcctcctgc tgctgctgct gctcctccgt cggtattatc 1920

-continued

```
gccgggcgga cggaagacaa cagtagcagg cgattcttgt gtctcacaac cgctctccac   1980
agatgcatgg ccagaaaatc cagcaggtac cccccgctca gatgggtttc ttcgctccat   2040
ttatccttta taaaactcaa aaaagcaaca gcagccgcag cgcgccccgg tgtggaaaaa   2100
tccaaagtct tgatgacctt ctcttggaaa agcgcctggt gacccagatt caaagaatca   2160
aacagctcac cacaggattt caaaagctct tcaaattccc acttgtaatc ctccttaatt   2220
ctgcagacta actttgcctg ggatgagccc cacagaaacc tccaaaacca agaggtactg   2280
ttagagctct gttccagcaa gttacgcaca gcagaaaaat cttccaaaca ctcccaagcc   2340
tccatgctcg accggtccct accgacgctg gtcgcgcctc ttatacccac gtagaacgca   2400
gctcagccaa tagaatgagt gccaatatgg aatttccagg ggaaaaccgg ggcggtgtta   2460
cgttttggct gccctttcac ttcccattga cgtgtattgg ctcgagaacg gtactttccc   2520
attaatcagc tatgggaaag taccgtttaa aggtcacgtt gcattagttt caatagccca   2580
ttgacgtcaa tggtgggaaa gtacatggcg ttttataaat ggctggaaaa acccaatgac   2640
tcacccctat tgaccttatg tacgtgccaa taatgggaaa aacccattga ctcacccccct   2700
attgaccttt tgtactgggc aaaacccaat ggaaagtccc tattgactca gtgtacttgg   2760
ctccaatggg actttcctgt tgattcaccc ctattgacct tatgtactgg gcaaaaccca   2820
ttggaaagtc cctaatgact cagtatatgg cggccgatac ttggcctcgg tggccgatga   2880
cctcgagggg gggcccggta cccggtggat gtggaatgtg tgcgaggcca gaggccactt   2940
gtgtagcgcc aagtgccagc ggggctgcta aagcgcatgc tccagactgc cttgggaaaa   3000
gcgcctcccc tacccggtag aattcgtaac caagattagc ccacggcgca ttatataccc   3060
tttaagcccc gccccattta acacgccatg caagttaaac attatctcac cctttattaa   3120
acttacatca actcattcag caaacaaagg cgttaaccac acacgcaatc acaggtttac   3180
accttatggc ctggggcgtt tacagctcaa gtccaaaggt tgcccaggct cgttaagcaa   3240
gtcctcgata cattccacag cctggcgacg cccaccaact ctcacggcaa ctggtttaat   3300
ggggcacagc gggaccaccg ggtgtatctc aggaggtgtg ttagaaggac cggagtcaca   3360
gctatccgta ctactattgc attctctaga cacaggtgat gtcgggcgtc tcaggatagc   3420
aggcgccatt ttaggacggc gggtaggtct tgcaggctcc ggttctggct cgggctcagg   3480
ctcaggttca gacacaggac cttttaaaaa aatcacaata caaaattctt taaaccacaa   3540
aactgtaaaa attaaaaaaa aaattaccac accaaaccca ccactctatc acccactgcc   3600
cataattttc acttactgta gacaaacatg ccacaggtcc tcatatagca aagcgaacac   3660
ataatatctg ggtcccccgt attcctccgg tgataatgac aagacctgca accgtgcccg   3720
gggtgctcca cataatctaa cacaaactcc tcaccctctt catcctcgtc gtcactgggt   3780
ggaaagccag cctcgtggca ggtaagatcg atcacctccg gtacaaggtt tggcatagaa   3840
accggaccca aggctctctg ctccggctgc tcgggctgcc gggaaaggtg aggcggctcc   3900
ggagaaccgg gcgccggcgg aaaagtgagt aagtcaatcc cttcctgcac cgccaacatt   3960
acagagtcgg gaaaaatctg cgaaaccgcc tcctcgttgg gatcttcggg ggccgtcacg   4020
tctaaatcat acagttcgtg aagggtaggt ggttcaaaat ggctaggagg tggaagatta   4080
tcagccagta cctcttcgat cagctggtcc aaaagactgg cggccatttc ttcggtaata   4140
acacctccgt ggcagataat atgtctcatt ttcagtcccg gtgtcggagc ggctcggagg   4200
agaaaactct actcgctggc actcaagagt ggcctcttga ggaactcacc gggtataaat   4260
acactacacg tcagctgact ataactcgag aacgagggag ccgactgccg acgtgcgctc   4320
```

```
cggaggcttg cagaatgcgg aacaccgcgc gggcaggaac agggcccaca ctaccgcccc   4380
acaccccgcc tcccgcaccg ccccttcccg gccgctgctc tcggcgcgcc ctgctgagca   4440
gccgctattg gccacagccc atcgcggtcg gcgcgctgcc attgctccct ggcgctgtcc   4500
gtctgcgagg gtactagtga gacgtgcggc ttccgtttgt cacgtccggc acgccgcgaa   4560
ccgcaaggaa ccttcccgac ttaggggcgg acgaggaagc gtcgccgggg ggcccacaag   4620
ggtagcggcg aagatccggg tgacgctgcg aacggacgtg aagaatgtgc gagacccagg   4680
gtcggcgccg ctgcgtttcc cggaaccacg cccagagcag ccgcgtccct gcgcaaaccc   4740
agggctgcct tggaaaaggc gcaaccccaa ccattaataa ctaatgcatg gcggtaatac   4800
ggttatccac agaatcaggg gataacgcag gaaagaacat ggtacggcag tttaaggttt   4860
acacctataa aagagagagc cgttatcgtc tgtttgtgga tgtacagagt gatattattg   4920
acacgccggg gcgacggatg gtgatccccc tggccagtgc acgtctgctg tcagataaag   4980
tctcccgtga actttacccg gtggtgcata tcggggatga aagctggcgc atgatgacca   5040
ccgatatggc cagtgtgccg gtctccgtta tcggggaaga agtggctgat ctcagccacc   5100
gcgaaaatga catcaaaaac gccattaacc tgatgttctg ggaatataa atgtcaggca   5160
tgagattatc aaaaaggatc ttcacctaga tccttttcac gtagaaagcc agtccgcaga   5220
aacggtgctg accccggatg aatgtcagct actgggctat ctggacaagg gaaaacgcaa   5280
gcgcaaagag aaagcaggta gcttgcagtg ggcttacatg gcgatagcta gactgggcgg   5340
ttttatggac agcaagcgaa ccggaattgc cagctggggc gccctctggt aaggttggga   5400
agccctgcaa agtaaactgg atggctttct cgccgccaag gatctgatgg cgcaggggat   5460
caagctctga tcaagagaca ggatgaggat cgtttcgcat gattgaacaa gatggattgc   5520
acgcaggttc tccggccgct tgggtggaga ggctattcgg ctatgactgg gcacaacaga   5580
caatcggctg ctctgatgcc gccgtgttcc ggctgtcagc gcaggggcgc ccggttcttt   5640
ttgtcaagac cgacctgtcc ggtgccctga atgaactgca agacgaggca gcgcggctat   5700
cgtggctggc cacgacgggc gttccttgcg cagctgtgct cgacgttgtc actgaagcgg   5760
gaagggactg gctgctattg ggcgaagtgc cggggcagga tctcctgtca tctcaccttg   5820
ctcctgccga gaaagtatcc atcatggctg atgcaatgcg gcggctgcat acgcttgatc   5880
cggctacctg cccattcgac caccaagcga aacatcgcat cgagcgagca cgtactcgga   5940
tggaagccgg tcttgtcgat caggatgatc tggacgaaga gcatcagggg ctcgcgccag   6000
ccgaactgtt cgccaggctc aaggcgagca tgcccgacgg cgaggatctc gtcgtgaccc   6060
atggcgatgc ctgcttgccg aatatcatgg tggaaaatgg ccgcttttct ggattcatcg   6120
actgtggccg gctgggtgtg gcggaccgct atcaggacat agcgttggct acccgtgata   6180
ttgctgaaga gcttggcggc gaatgggctg accgcttcct cgtgctttac ggtatcgccg   6240
ctcccgattc gcagcgcatc gccttctatc gccttcttga cgagttcttc tgaattatta   6300
acgcttacaa tttcctgatg cggtattttc tccttacgca tctgtgcggt atttcacacc   6360
gcatacaggt ggcacttttc ggggaaatgt gcgcggaacc cctatttgtt tatttttcta   6420
aatacattca aatatgtatc cgctcatgag acaataaccc tgataaatgc ttcaataata   6480
ttgaaaaagg aagagtatga gtattcaaca tttccgtgtc gcccttattc ccttttttgc   6540
ggcattttgc cttcctgttt ttgctcaccc agaaacgctg gtgaaagtaa aagatgctga   6600
agatcagttg ggtgcacgag tgggttacat cgaactggat ctcaacagcg gtaagatcct   6660
tgagagtttt cgccccgaag aacgttttcc aatgatgagc acttttaaag ttctgctatg   6720
```

```
tggcgcggta ttatcccgta ttgacgccgg gcaagagcaa ctcggtcgcc gcatacacta   6780

ttctcagaat gacttggttg agtactcacc agtcacagaa aagcatctta cggatggcat   6840

gacagtaaga gaattatgca gtgctgccat aaccatgagt gataacactg cggccaactt   6900

acttctgaca acgatcggag gaccgaagga gctaaccgct tttttgcaca acatggggga   6960

tcatgtaact cgccttgatc gttgggaacc ggagctgaat gaagccatac caaacgacga   7020

gcgtgacacc acgatgcctg tagcaatggc aacaacgttg cgcaaactat taactggcga   7080

actacttact ctagcttccc ggcaacaatt aatagactgg atggaggcgg ataaagttgc   7140

aggaccactt ctgcgctcgg cccttccggc tggctggttt attgctgata aatctggagc   7200

cggtgagcgt gggtctcgcg gtatcattgc agcactgggg ccagatggta agccctcccg   7260

tatcgtagtt atctacacga cggggagtca ggcaactatg gatgaacgaa atagacagat   7320

cgctgagata ggtgcctcac tgattaagca ttggtaactg tcagaccaag tttactcata   7380

tatactttag attgatttaa aacttcattt ttaatttaaa aggatctagg tgaagatcct   7440

ttttgataat ctcatgacca aaatccctta acgtgagttt tcgttccact gagcgtcaga   7500

ccccgtagaa aagatcaaag gatcttcttg agatcctttt tttctgcgcg taatctgctg   7560

cttgcaaaca aaaaaaccac cgctaccagc ggtggtttgt ttgccggatc aagagctacc   7620

aactcttttt ccgaaggtaa ctggcttcag cagagcgcag ataccaaata ctgtccttct   7680

agtgtagccg tagttaggcc accacttcaa gaactctgta gcaccgccta catacctcgc   7740

tctgctaatc ctgttaccag tggctgctgc cagtggcgat aagtcgtgtc ttaccgggtt   7800

ggactcaaga cgatagttac cggataaggc gcagcggtcg ggctgaacgg ggggttcgtg   7860

cacacagccc agcttggagc gaacgaccta caccgaactg agatacctac agcgtgagct   7920

atgagaaagc gccacgcttc ccgaagggag aaaggcggac aggtatccgg taagcggcag   7980

ggtcggaaca ggagagcgca cgagggagct tccaggggga aacgcctggt atctttatag   8040

tcctgtcggg tttcgccacc tctgacttga gcgtcgattt ttgtgatgct cgtcaggggg   8100

gcggagccta tggaaaaacg ccagcaacgc ggccttttta cggttcctgg ccttttgctg   8160

gccttttgct cacatgttct ttcctgcgtt atcccctgat tctgtggata accgtattac   8220

cgcctttgag tgagctgata ccgctcgccg cagccgaacg accgagcgca gcgagtcagt   8280

gagcgaggaa gcggaag                                                  8297
```

```
<210> SEQ ID NO 10
<211> LENGTH: 7174
<212> TYPE: DNA
<213> ORGANISM: Artificial Sequence
<220> FEATURE:
<223> OTHER INFORMATION: Description of Artificial Sequence: Plasmid 25F

<400> SEQUENCE: 10

agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagctca    240

gaattaaccc tcactaaagg gactagtcct gcaggtttaa acgaattcgc ccttaatctt    300

aagctcggga gtagcggatg ccccggggag aggagtgtta gtaaccgcga cgctggtggg    360

ggtcggcttg ttaagagggg cgctgctaac gctgcaagag tgggttgtca gcgtggggcc    420

ggtgctactg gaatcgatac cggcatgatt gacagcctgg gcgaggatgt cacctgatgg    480
```

-continued

```
tgataagaag acacgggaga cttagtacgg tttcacaggc gtgacacgtt tattgagtag    540
gattacagag tataacatag agtataatat agagtataca atagtgacgt gggatccgtt    600
aacaggtgaa ccatttatac agtctcacgt ctctttattg catacgctcc gctaaatgtt    660
tccattcgct catttgccag taatacagca gattcgcaaa ctcactgaac caatcttctg    720
tataaaaatg tacgcgctgc gtgtccaaat caacatcaat tttcctcata tacagacagg    780
ggctgccacc cgcctccccc aagcgcgaca ccgcaattag gaatggtagc ctgctgtgca    840
ggtccacgtg aattaacatc ccgcacacgt tcccgatcgg tcgctgcata aatactggag    900
agaaatcgct aaaccccggt gacgcccaca tagccacgaa gtacacccct gccacattca    960
agtcatcctc caacctggcc caaacataag tggccaaatc ggaaggagcc aggtggcaag   1020
ccgataaccc catacgatgc aaaggtaacc cgtggcaagc gcatcccccg aaatgaagtt   1080
cgaaagaatc gtaacacagt agctgatagg catgaagcgg cgtcggcatc tgaagaccgt   1140
catcatcttc gtcgtcttcc atgtcatccc caacttcctc ctcgcgctcc gcttcctgtt   1200
ggcggcgctg ctggtgctgc agcaccatct ccaggatctg ctcgtcgttc atcttaatcc   1260
ggactcgaga aaggcccgga gatgaggaag aggagaacag cgcggcagac gtgcgctttt   1320
gaagcgtgcg agaatgccgg gcctccggag gaccttcggg cgcccgcccc gcccctgagc   1380
ccgcccctga gcccgccccc ggacccaccc cttcccagcc tctgagccca gaaagcgaag   1440
gagcaaagct gctattggcc gctgccccaa aggcctaccc gcttccattg ctcagcggtg   1500
ctgtccatct gcacgagact agtgagacgt gctacttcca tttgtcacgt cctgcacgac   1560
gcgagctgcg gggcgggggg gaacttcctg actaggggag gagtagaagg tggcgcgaag   1620
gggccaccaa agaacggagc cggttggcgc ctaccggtgg atgtggaatg tgtgcgaggc   1680
cagaggccac ttgtgtagcg ccaagtgcca gcggggctgc taaagcgcat gctccagact   1740
gccttgggaa aagcgcctcc cctacccggt agaattcgcg gcctcgacgg cctcggtggc   1800
cagtctagtc aataatcaat gtccgagctc gaatacactc cgctatcgct acgtgactgg   1860
gtcatggctg cgccccgaca cccgccaaca cccgctgacg cgccctgacg ggcttgtctg   1920
ctcccggcat ccgcttacag acaagctgtg accgtctccg ggagctgcat gtgtcagagg   1980
ttttcaccgt catcaccgaa acgcgcgagg cagccggatc ataatcagcc ataccacatt   2040
tgtagaggtt ttacttgctt taaaaaacct cccacacctc cccctgaacc tgaaacataa   2100
aatgaatgca attgttgttg ttaacttgtt tattgcagct tataatggtt acaaataaag   2160
caatagcatc acaaatttca caaataaagc atttttttca ctgcattcta gttgtggttt   2220
gtccaaactc atcaatgtat cttatcatgt ctggatcgaa gctctagagc ggccaacttc   2280
agggattggt tacagagaat ggtaggggtg gtgccgagac ccgagtcccc gcctactcat   2340
acgtaggcag gtttccatga cacccagtct tgcccaatct tggagagaat ggggatttct   2400
gggttcattt ctctcggggg cggggctatc cccgccgaga gtcatacacc aaatttctgt   2460
agaaaacgga tttttgccag tcttgatggc acaaacttcg ggagtttggt taaaaaatcg   2520
gctgaagaat ggttctggaa gtgttctttt cagatctttt ttggtgaaaa ctccagtggt   2580
caggagccga tattgtcggg gggctttgat ggtggtggtc ccacagagac cctcatagcc   2640
agggaccccc actccgcgag ggacatggat cttcagtgtg tctagcgcca tcttcagggc   2700
atgcacggaa ccaatgggga agcccaggtc ccccacgtgg gttatgccgt gggggagggg   2760
atccgagtat tccctggcca cccaatcagg aaccgcgaac gcgccacgga ccgccttctc   2820
catcataatg agggcctcac tgggggtctt gggttccgcg gagcgccccc taatggtaac   2880
```

-continued

```
gtggataatg cgctggggac cctcgtagtc tgcgaagatt gcctttctcc ccatggacac   2940
tagggggctg aatgagtatt cccgcagttg ctcgccggtc aggttagggt taaaaatcag   3000
gccggtggtc accatttctc taaggctagt ggtgggattc cgctggctag ggtccacagg   3060
gaccaccgaa gtaaaggaaa tggtccccat gtagtatgga aggtccccag ggaacatgcg   3120
gaatgggttg cgggccatac ctgtagaatg tacagggggg tctcgagaac gagggagccg   3180
actgccgacg tgcgctccgg aggcttgcag aatgcggaac accgcgcggg caggaacagg   3240
gcccacacta ccgccccaca ccccgcctcc cgcaccgccc cttcccggcc gctgctctcg   3300
gcgcgccctg ctgagcagcc gctattggcc acagcccatc gcggtcggcg cgctgccatt   3360
gctccctggc gctgtccgtc tgcgagggta ctagtgagac gtgcggcttc cgtttgtcac   3420
gtccggcacg ccgcgaaccg caaggaacct tcccgactta ggggcggacg aggaagcgtc   3480
gccggggggc ccacaagggt agcggcgaag atccgggtga cgctgcgaac ggacgtgaag   3540
aatgtgcgag acccagggtc ggcgccgctg cgtttcccgg aaccacgccc agagcagccg   3600
cgtccctgcg caaacccagg gctgccttgg aaaaggcgca accccaacca ttaataacta   3660
atgcatggcg gtaatacggt tatccacaga atcaggggat aacgcaggaa agaacatggt   3720
acggcagttt aaggtttaca cctataaaag agagagccgt tatcgtctgt ttgtggatgt   3780
acagagtgat attattgaca cgccggggcg acggatggtg atccccctgg ccagtgcacg   3840
tctgctgtca gataaagtct cccgtgaact ttacccggtg gtgcatatcg gggatgaaag   3900
ctggcgcatg atgaccaccg atatggccag tgtgccggtc tccgttatcg gggaagaagt   3960
ggctgatctc agccaccgcg aaaatgacat caaaaacgcc attaacctga tgttctgggg   4020
aatataaatg tcaggcatga gattatcaaa aaggatcttc acctagatcc ttttcacgta   4080
gaaagccagt ccgcagaaac ggtgctgacc ccggatgaat gtcagctact gggctatctg   4140
gacaagggaa aacgcaagcg caaagagaaa gcaggtagct tgcagtgggc ttacatggcg   4200
atagctagac tgggcggttt tatggacagc aagcgaaccg gaattgccag ctggggcgcc   4260
ctctggtaag gttgggaagc cctgcaaagt aaactggatg gctttctcgc cgccaaggat   4320
ctgatggcgc aggggatcaa gctctgatca agagacagga tgaggatcgt ttcgcatgat   4380
tgaacaagat ggattgcacg caggttctcc ggccgcttgg gtggagaggc tattcggcta   4440
tgactgggca caacagacaa tcggctgctc tgatgccgcc gtgttccggc tgtcagcgca   4500
ggggcgcccg gttctttttg tcaagaccga cctgtccggt gccctgaatg aactgcaaga   4560
cgaggcagcg cggctatcgt ggctggccac gacgggcgtt ccttgcgcag ctgtgctcga   4620
cgttgtcact gaagcgggaa gggactggct gctattgggc gaagtgccgg ggcaggatct   4680
cctgtcatct caccttgctc ctgccgagaa agtatccatc atggctgatg caatgcggcg   4740
gctgcatacg cttgatccgg ctacctgccc attcgaccac caagcgaaac atcgcatcga   4800
gcgagcacgt actcggatgg aagccggtct tgtcgatcag gatgatctgg acgaagagca   4860
tcaggggctc gcgccagccg aactgttcgc caggctcaag gcgagcatgc ccgacggcga   4920
ggatctcgtc gtgacccatg gcgatgcctg cttgccgaat atcatggtgg aaaatggccg   4980
cttttctgga ttcatcgact gtggccggct gggtgtggcg gaccgctatc aggacatagc   5040
gttggctacc cgtgatattg ctgaagagct tggcggcgaa tgggctgacc gcttcctcgt   5100
gctttacggt atcgccgctc ccgattcgca gcgcatcgcc ttctatcgcc ttcttgacga   5160
gttcttctga attattaacg cttacaattt cctgatgcgg tattttctcc ttacgcatct   5220
gtgcggtatt tcacaccgca tacaggtggc acttttcggg gaaatgtgcg cggaacccct   5280
```

```
atttgtttat ttttctaaat acattcaaat atgtatccgc tcatgagaca ataaccctga   5340
taaatgcttc aataatattg aaaaaggaag agtatgagta ttcaacattt ccgtgtcgcc   5400
cttattccct tttttgcggc attttgcctt cctgtttttg ctcacccaga aacgctggtg   5460
aaagtaaaag atgctgaaga tcagttgggt gcacgagtgg gttacatcga actggatctc   5520
aacagcggta agatccttga gagttttcgc cccgaagaac gttttccaat gatgagcact   5580
tttaaagttc tgctatgtgg cgcggtatta tcccgtattg acgccgggca agagcaactc   5640
ggtcgccgca tacactattc tcagaatgac ttggttgagt actcaccagt cacagaaaag   5700
catcttacgg atggcatgac agtaagagaa ttatgcagtg ctgccataac catgagtgat   5760
aacactgcgg ccaacttact tctgacaacg atcggaggac cgaaggagct aaccgctttt   5820
ttgcacaaca tgggggatca tgtaactcgc cttgatcgtt gggaaccgga gctgaatgaa   5880
gccataccaa acgacgagcg tgacaccacg atgcctgtag caatggcaac aacgttgcgc   5940
aaactattaa ctggcgaact acttactcta gcttcccggc aacaattaat agactggatg   6000
gaggcggata aagttgcagg accacttctg cgctcggccc ttccggctgg ctggtttatt   6060
gctgataaat ctggagccgg tgagcgtggg tctcgcggta tcattgcagc actggggcca   6120
gatggtaagc cctcccgtat cgtagttatc tacacgacgg ggagtcaggc aactatggat   6180
gaacgaaata gacagatcgc tgagataggt gcctcactga ttaagcattg gtaactgtca   6240
gaccaagttt actcatatat actttagatt gatttaaaac ttcattttta atttaaaagg   6300
atctaggtga agatcctttt tgataatctc atgaccaaaa tcccttaacg tgagttttcg   6360
ttccactgag cgtcagaccc cgtagaaaag atcaaaggat cttcttgaga tccttttttt   6420
ctgcgcgtaa tctgctgctt gcaaacaaaa aaaccaccgc taccagcggt ggtttgtttg   6480
ccggatcaag agctaccaac tctttttccg aaggtaactg gcttcagcag agcgcagata   6540
ccaaatactg tccttctagt gtagccgtag ttaggccacc acttcaagaa ctctgtagca   6600
ccgcctacat acctcgctct gctaatcctg ttaccagtgg ctgctgccag tggcgataag   6660
tcgtgtctta ccgggttgga ctcaagacga tagttaccgg ataaggcgca gcggtcgggc   6720
tgaacggggg gttcgtgcac acagcccagc ttggagcgaa cgacctacac cgaactgaga   6780
tacctacagc gtgagctatg agaaagcgcc acgcttcccg aagggagaaa ggcggacagg   6840
tatccggtaa gcggcagggt cggaacagga gagcgcacga gggagcttcc agggggaaac   6900
gcctggtatc tttatagtcc tgtcgggttt cgccacctct gacttgagcg tcgatttttg   6960
tgatgctcgt caggggggcg gagcctatgg aaaaacgcca gcaacgcggc ctttttacgg   7020
ttcctgggct tttgctggcc ttttgctcac atgttctttc ctgcgttatc ccctgattct   7080
gtggataacc gtattaccgc ctttgagtga gctgataccg ctcgccgcag ccgaacgacc   7140
gagcgcagcg agtcagtgag cgaggaagcg gaag                               7174

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer V206

<400> SEQUENCE: 11

aacctcgaga ccccctgta cattcta                                          27
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer V207

<400> SEQUENCE: 12
gccgttaact tcagggattg gttacag 27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer V208

<400> SEQUENCE: 13
cacctcgagt ccggattaag atgaacg 27

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Primer V209

<400> SEQUENCE: 14
ccagttaaca ggtgaaccat ttatacag 28

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: RT primer

<400> SEQUENCE: 15
gcctttgaga gttactcttt g 21

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: primer cDNA 1

<400> SEQUENCE: 16
aaacactgta cggcacccgc att 23

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer cDNA 2

<400> SEQUENCE: 17
gcctttgaga gttactcttt g 21

<210> SEQ ID NO 18
<211> LENGTH: 8681
<212> TYPE: DNA
<213> ORGANISM: Artificial Sequence
<220> FEATURE:
<223> OTHER INFORMATION: Description of Artificial Sequence: Plasmid 60E

<400> SEQUENCE: 18

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagctca    240
gaattaaccc tcactaaagg gactagtcct gcaggtttct agtcctgcag gtttaaacga    300
attcgccctt aatcttaagc tgccgccccg acgttggctg cgagccctgg gccttcaccc    360
gaacttgggg ggtggggtgg ggaaaaggaa gaaacgcggg cgtattggcc ccaatggggt    420
ctcggtgggg tatcgacaga gtgccagccc tgggaccgaa ccccgcgttt atgaacaaac    480
gacccaacac cgtgcgtttt attctgtctt tttattgccg tcatagcgcg ggttccttcc    540
ggtattgtct ccttccgtgt tatcctcaat ctgtatcttc atcgctagag ccaaactcag    600
cgcgggtgca ggccagcacc aagtgatcgg gcctcagctc ctcggtcaca tccagcatca    660
caggctggtt cctaatatgt ttaccgccac actcgcaggg tctgcacctg gtgcgggtct    720
catcgtacct cagcaccttc cagatcttca tggtcatgtc aaacaccccg ttcaggttca    780
ccttggacat gctctcgggc tcaagcaata tcttagtgtg actcaaattg cattggtaag    840
gtaggaacac ccccctcctg ttacccaaat gcaaggaaca gcgggtcagt atgttatgct    900
caaacactgg ccaggccttg cgagagtggc tggctacgtg aatggtcttc agcaggtgac    960
agttgccgtc cgagcaggtc agcatctgag aggccctgtc ctcgcagttg ccacatacca   1020
tgttatgctt aatcacagcc acgcttttca ctagcatgaa gcaaccacag tcggaggcca   1080
cattgtggcg caccctggag ttaccctcag acaggatacc caaggtacac ctttcaaaga   1140
ggcatttctt aattgaagcc ctgcttttgg ggcgacacac cacccccttc cagcagcagt   1200
aaaaggcaca gccccgaacc cttacatcgg tccaggcttc cacacaggta ttgttaaacc   1260
catagaagct tacaccgtgt aggataaggt tggtattggc caggaaaacc gtaccgctaa   1320
aattggggcc agtaaacctt acattcataa taaccacccc gtccatgcca agcacccccg   1380
gccacatatt tatcatgcta catctaaagg ccaccctatc ctccgtatct atctccacct   1440
cggccccgtt cccagaaatg tagcaacaat tcctgatatt tacaagtttg ctgatcttgt   1500
acttgcaatc tggcctaagt gccacctttg catataccct aatagcctcc tcaaaatcat   1560
cccctggctg cagccagtaa gtggtcagct gctctatgga atacttctgc gccagcagat   1620
caagctcatt agcgcaatta tccttgatct gttgaaaagt aatacactca ggacggtgtc   1680
tggtcattaa gctaaaagct agattcctag cctcctctgt agcctcacaa gcccccccgct   1740
ccctctttac cccctttagc cctgcccat cctctgtaat tgtcaaaatg cgtctcagtt   1800
ctggatacag ttcagccacc tgtacaacat tcattcccga gggtccaggc cggctctcgg   1860
gttccatggg ctctgctcct gccgccgccg cctggcttcc tcctgctgct gctgctgctc   1920
ctccgtcggt attatcgccg ggcggacgga agacaacagt agcaggcgat tcttgtgtct   1980
cacaaccgct ctccacagat gcatggccag aaaatccagc aggtaccccc cgctcagatg   2040
ggtttcttcg ctccatttat cctttataaa actcaaaaaa gcaacagcag ccgcagcgcg   2100
ccccggtgtg gaaaaatcca aagtcttgat gaccttctct tggaaaagcg cctggtgacc   2160
cagattcaaa gaatcaaaca gctcaccaca ggatttcaaa agctcttcaa attcccactt   2220
```

```
gtaatcctcc ttaattctgc agactaactt tgcctgggat gagccccaca gaaacctcca   2280
aaaccaagag gtactgttag agctctgttc cagcaagtta cgcacagcag aaaaatcttc   2340
caaacactcc caagcctcca tgctcgagat ccttcctcct cgggcgggtg tggaccaccg   2400
cctcgcctct ctccggaaaa aaaaaatgaa ataaacaaca aaaccgaaca aaagcgaaac   2460
gccacggatg gagcgcaaaa ccctcttcga agttctgcga ctgcacacag acagtcaaat   2520
ggagcagagc caggcgagcg accgcccgag ccgcagtagc gcgcaggtct ggggaagaga   2580
ggcgcaggta ggggatctga gtccggtagc gatctgcggc acgctgttga cgctgttaag   2640
cgggtcgctg cagggtcgct cggtattcga ggccacacgc gtcaccttaa tatgcgaagt   2700
ggacctggga ccgcgccgcc ccgactgcat ctgcgtgttc gaattcgcca atgacaagac   2760
gctgggcggg gtttgtgtca tcatagaact aaagacatgc aaatatattt cttccgggga   2820
caccgccagc aaacgcgagc aacgggccac ggggatgaag cagctgcgcc actccctgaa   2880
gctcctgcag tccctcgcgc ctccgggtga caagatagtg tacctgtgcc ccgtcctggt   2940
gtttgtcgcc caacggacgc tccgcgtcag ccgcgtgacc cggctcgtcc cgcagaaggt   3000
ctccggtaat atcaccgcag tcgtgcggat gctccagagc ctgtccacgt atacggtccc   3060
cattgagcct aggacccagc gagcccgtcg ccgccgcggc ggcgccgccc gggggtctgc   3120
gagcagaccg aaaaggtcac actctggggc gcgcgacccg cccgagtcag cggcccgcca   3180
gttaccaccc gccgaccaaa cccccacctc cacggagggc ggggggggtgc ttaagaggat   3240
cgcggcgctc ttctgcgtgc ccgtggccac caagaccaaa ccccgagccg cctccgaatg   3300
agagtgtttc gttccttccc cctccccccg cgtcagacaa accctaacca ccgcttaagc   3360
ggcccccgcg aggtccgaag actcatttgg atccactaga aacgaattcg taaccaagat   3420
tagcccacgg cgcattatat accctttaag ccccgcccca tttaacacgc catgcaagtt   3480
aaacattatc tcacccttta ttaaacttac atcaactcat tcagcaaaca aaggcgttaa   3540
ccacacacgc aatcacaggt ttacacctta tggcctgggg cgtttacagc tcaagtccaa   3600
aggttgccca ggctcgttaa gcaagtcctc gatacattcc acagcctggc gacgcccacc   3660
aactctcacg gcaactggtt taatggggca cagcgggacc accgggtgta tctcaggagg   3720
tgtgttagaa ggaccggagt cacagctatc cgtactacta ttgcattctc tagacacagg   3780
tgatgtcggg cgtctcagga tagcaggcgc cattttagga cggcgggtag gtcttgcagg   3840
ctccggttct ggctcgggct caggctcagg ttcagacaca ggacctttta aaaaaatcac   3900
aatacaaaat tctttaaacc acaaaactgt aaaaattaaa aaaaaaatta ccacaccaaa   3960
cccaccactc tatcacccac tgcccataat tttcacttac tgtagacaaa catgccacag   4020
gtcctcatat agcaaagcga acacataata tctgggtccc ccgtattcct ccggtgataa   4080
tgacaagacc tgcaaccgtg cccggggtgc tccacataat ctaacacaaa ctcctcaccc   4140
tcttcatcct cgtcgtcact gggtggaaag ccagcctcgt ggcaggtaag atcgatcacc   4200
tccggtacaa ggtttggcat agaaaccgga cccaaggctc tctgctccgg ctgctcgggc   4260
tgccgggaaa ggtgaggcgg ctccggagaa ccgggcgccg gcggaaaagt gagtaagtca   4320
atcccttcct gcaccgccaa cattacagag tcgggaaaaa tctgcgaaac cgcctcctcg   4380
ttgggatctt cgggggccgt cacgtctaaa tcatacagtt cgtgaagggt aggtggttca   4440
aaatggctag gaggtggaag attatcagcc agtacctctt cgatcagctg gtccaaaaga   4500
ctggcggcca tttcttcggt aataacacct ccgtggcaga taatatgtct cattttcagt   4560
cccggtgtcg gagcggctcg gaggagaaaa ctctactcgc tggcactcaa gagtggcctc   4620
```

-continued

```
ttgaggaact caccgggtat aaatacacta cacgtcagct gactataact cgagaacgag   4680
ggagccgact gccgacgtgc gctccggagg cttgcagaat gcggaacacc gcgcgggcag   4740
gaacagggcc cacactaccg ccccacaccc cgcctcccgc accgcccctt cccggccgct   4800
gctctcggcg cgccctgctg agcagccgct attggccaca gcccatcgcg gtcggcgcgc   4860
tgccattgct ccctggcgct gtccgtctgc gagggtacta gtgagacgtg cggcttccgt   4920
ttgtcacgtc cggcacgccg cgaaccgcaa ggaaccttcc cgacttaggg gcggacgagg   4980
aagcgtcgcc ggggggccca caagggtagc ggcgaagatc cgggtgacgc tgcgaacgga   5040
cgtgaagaat gtgcgagacc cagggtcggc gccgctgcgt ttcccggaac cacgcccaga   5100
gcagccgcgt ccctgcgcaa acccagggct gccttggaaa aggcgcaacc ccaaccatta   5160
ataactaatg catggcggta atacggttat ccacagaatc aggggataac gcaggaaaga   5220
acatggtacg gcagtttaag gtttacacct ataaaagaga gagccgttat cgtctgtttg   5280
tggatgtaca gagtgatatt attgacacgc cggggcgacg gatggtgatc cccctggcca   5340
gtgcacgtct gctgtcagat aaagtctccc gtgaacttta cccggtggtg catatcgggg   5400
atgaaagctg gcgcatgatg accaccgata tggccagtgt gccggtctcc gttatcgggg   5460
aagaagtggc tgatctcagc caccgcgaaa atgacatcaa aaacgccatt aacctgatgt   5520
tctggggaat ataaatgtca ggcatgagat tatcaaaaag gatcttcacc tagatccttt   5580
tcacgtagaa agccagtccg cagaaacggt gctgaccccg gatgaatgtc agctactggg   5640
ctatctggac aagggaaaac gcaagcgcaa agagaaagca ggtagcttgc agtgggctta   5700
catggcgata gctagactgg gcggttttat ggacagcaag cgaaccggaa ttgccagctg   5760
gggcgccctc tggtaaggtt gggaagccct gcaaagtaaa ctggatggct ttctcgccgc   5820
caaggatctg atggcgcagg ggatcaagct ctgatcaaga gacaggatga ggatcgtttc   5880
gcatgattga acaagatgga ttgcacgcag gttctccggc cgcttgggtg gagaggctat   5940
tcggctatga ctgggcacaa cagacaatcg gctgctctga tgccgccgtg ttccggctgt   6000
cagcgcaggg gcgcccggtt ctttttgtca agaccgacct gtccggtgcc ctgaatgaac   6060
tgcaagacga ggcagcgcgg ctatcgtggc tggccacgac gggcgttcct tgcgcagctg   6120
tgctcgacgt tgtcactgaa gcgggaaggg actggctgct attgggcgaa gtgccggggc   6180
aggatctcct gtcatctcac cttgctcctg ccgagaaagt atccatcatg gctgatgcaa   6240
tgcggcggct gcatacgctt gatccggcta cctgcccatt cgaccaccaa gcgaaacatc   6300
gcatcgagcg agcacgtact cggatggaag ccggtcttgt cgatcaggat gatctggacg   6360
aagagcatca ggggctcgcg ccagccgaac tgttcgccag gctcaaggcg agcatgcccg   6420
acggcgagga tctcgtcgtg acccatggcg atgcctgctt gccgaatatc atggtggaaa   6480
atggccgctt ttctggattc atcgactgtg gccggctggg tgtggcggac cgctatcagg   6540
acatagcgtt ggctacccgt gatattgctg aagagcttgg cggcgaatgg gctgaccgct   6600
tcctcgtgct ttacggtatc gccgctcccg attcgcagcg catcgccttc tatcgccttc   6660
ttgacgagtt cttctgaatt attaacgctt acaatttcct gatgcggtat tttctcctta   6720
cgcatctgtg cggtatttca caccgcatac aggtggcact tttcggggaa atgtgcgcgg   6780
aacccctatt tgtttatttt tctaaataca ttcaaatatg tatccgctca tgagacaata   6840
accctgataa atgcttcaat aatattgaaa aaggaagagt atgagtattc aacatttccg   6900
tgtcgccctt attccctttt ttgcggcatt ttgccttcct gtttttgctc acccagaaac   6960
gctggtgaaa gtaaaagatg ctgaagatca gttgggtgca cgagtgggtt acatcgaact   7020
```

```
ggatctcaac agcggtaaga tccttgagag ttttcgcccc gaagaacgtt ttccaatgat   7080

gagcactttt aaagttctgc tatgtggcgc ggtattatcc cgtattgacg ccgggcaaga   7140

gcaactcggt cgccgcatac actattctca gaatgacttg gttgagtact caccagtcac   7200

agaaaagcat cttacggatg gcatgacagt aagagaatta tgcagtgctg ccataaccat   7260

gagtgataac actgcggcca acttacttct gacaacgatc ggaggaccga aggagctaac   7320

cgcttttttg cacaacatgg gggatcatgt aactcgcctt gatcgttggg aaccggagct   7380

gaatgaagcc ataccaaacg acgagcgtga caccacgatg cctgtagcaa tggcaacaac   7440

gttgcgcaaa ctattaactg gcgaactact tactctagct tcccggcaac aattaataga   7500

ctggatggag gcggataaag ttgcaggacc acttctgcgc tcggcccttc cggctggctg   7560

gtttattgct gataaatctg gagccggtga gcgtgggtct cgcggtatca ttgcagcact   7620

ggggccagat ggtaagccct cccgtatcgt agttatctac acgacgggga gtcaggcaac   7680

tatggatgaa cgaaatagac agatcgctga gataggtgcc tcactgatta agcattggta   7740

actgtcagac caagtttact catatatact ttagattgat ttaaaacttc atttttaatt   7800

taaaaggatc taggtgaaga tcctttttga taatctcatg accaaaatcc cttaacgtga   7860

gttttcgttc cactgagcgt cagaccccgt agaaaagatc aaaggatctt cttgagatcc   7920

tttttttctg cgcgtaatct gctgcttgca aacaaaaaaa ccaccgctac cagcggtggt   7980

ttgtttgccg gatcaagagc taccaactct ttttccgaag gtaactggct tcagcagagc   8040

gcagatacca aatactgtcc ttctagtgta gccgtagtta ggccaccact tcaagaactc   8100

tgtagcaccg cctacatacc tcgctctgct aatcctgtta ccagtggctg ctgccagtgg   8160

cgataagtcg tgtcttaccg ggttggactc aagacgatag ttaccggata aggcgcagcg   8220

gtcgggctga acggggggtt cgtgcacaca gcccagcttg gagcgaacga cctacaccga   8280

actgagatac ctacagcgtg agctatgaga aagcgccacg cttcccgaag ggagaaaggc   8340

ggacaggtat ccggtaagcg gcagggtcgg aacaggagag cgcacgaggg agcttccagg   8400

gggaaacgcc tggtatcttt atagtcctgt cgggtttcgc cacctctgac ttgagcgtcg   8460

atttttgtga tgctcgtcag gggggcggag cctatggaaa aacgccagca acgcggcctt   8520

tttacggttc ctgggctttt gctggccttt tgctcacatg ttctttcctg cgttatcccc   8580

tgattctgtg gataaccgta ttaccgcctt tgagtgagct gataccgctc gccgcagccg   8640

aacgaccgag cgcagcgagt cagtgagcga ggaagcggaa g                       8681
```

```
<210> SEQ ID NO 19
<211> LENGTH: 5428
<212> TYPE: DNA
<213> ORGANISM: Artificial Sequence
<220> FEATURE:
<223> OTHER INFORMATION: Description of Artificial Sequence: Plasmid 36E

<400> SEQUENCE: 19

tcttccgctt cctcgctcac tgactcgctg cgctcggtcg ttcggctgcg gcgagcggta     60

tcagctcact caaaggcggt aatacggtta tccacagaat caggggataa cgcaggaaag    120

aacatgtgag caaaaggcca gcaaaagccc aggaaccgta aaaaggccgc gttgctggcg    180

tttttccata ggctccgccc ccctgacgag catcacaaaa atcgacgctc aagtcagagg    240

tggcgaaacc cgacaggact ataaagatac caggcgtttc cccctggaag ctccctcgtg    300

cgctctcctg ttccgaccct gccgcttacc ggatacctgt ccgcctttct cccttcggga    360

agcgtggcgc tttctcatag ctcacgctgt aggtatctca gttcggtgta ggtcgttcgc    420
```

-continued

```
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgtatgcgg tgtgaaatac cgcacagatg cgtaaggaga aaataccgca   1980
tcaggaaatt gtaagcgtta ataattcaga agaactcgtc aagaaggcga tagaaggcga   2040
tgcgctgcga atcgggagcg gcgataccgt aaagcacgag gaagcggtca gcccattcgc   2100
cgccaagctc ttcagcaata tcacgggtag ccaacgctat gtcctgatag cggtccgcca   2160
cacccagccg gccacagtcg atgaatccag aaaagcggcc attttccacc atgatattcg   2220
gcaagcaggc atcgccatgg gtcacgacga gatcctcgcc gtcgggcatg ctcgccttga   2280
gcctggcgaa cagttcggct ggcgcgagcc cctgatgctc ttcgtccaga tcatcctgat   2340
cgacaagacc ggcttccatc cgagtacgtg ctcgctcgat gcgatgtttc gcttggtggt   2400
cgaatgggca ggtagccgga tcaagcgtat gcagccgccg cattgcatca gccatgatgg   2460
atactttctc ggcaggagca aggtgagatg acaggagatc ctgccccggc acttcgccca   2520
atagcagcca gtcccttccc gcttcagtga caacgtcgag cacagctgcg caaggaacgc   2580
ccgtcgtggc cagccacgat agccgcgctg cctcgtcttg cagttcattc agggcaccgg   2640
acaggtcggt cttgacaaaa agaaccgggc gcccctgcgc tgacagccgg aacacggcgg   2700
catcagagca gccgattgtc tgttgtgccc agtcatagcc gaatagcctc tccacccaag   2760
cggccggaga acctgcgtgc aatccatctt gttcaatcat gcgaaacgat cctcatcctg   2820
```

-continued

```
tctcttgatc agagcttgat cccctgcgcc atcagatcct tggcggcgag aaagccatcc   2880
agtttacttt gcagggcttc ccaaccttac cagagggcgc cccagctggc aattccggtt   2940
cgcttgctgt ccataaaacc gcccagtcta gctatcgcca tgtaagccca ctgcaagcta   3000
cctgctttct ctttgcgctt gcgttttccc ttgtccagat agcccagtag ctgacattca   3060
tccggggtca gcaccgtttc tgcggactgg ctttctacgt gaaaaggatc taggtgaaga   3120
tcctttttga taatctcatg cctgacattt atattcccca gaacatcagg ttaatggcgt   3180
tttgatgtc attttcgcgg tggctgagat cagccacttc ttccccgata acggagaccg   3240
gcacactggc catatcggtg gtcatcatgc gccagctttc atccccgata tgcaccaccg   3300
ggtaaagttc acgggagact ttatctgaca gcagacgtgc actggccagg gggatcacca   3360
tccgtcgccc cggcgtgtca ataatatcac tctgtacatc cacaaacaga cgataacggc   3420
tctctctttt ataggtgtaa accttaaact gccgtacgta taggctgcgc aactgttggg   3480
aagggcgatc ggtgcgggcc tcttcgctat tacgccagct ggcgaaaggg ggatgtgctg   3540
caaggcgatt aagttgggta acgccagggt tttcccagtc acgacgttgt aaaacgacgg   3600
ccagtgaatt gtaatacgac tcactatagg gcgaattgaa tttagcggcc gcgaattcta   3660
ccgggtaggg gaggcgcttt tcccaaggca gtctggagca tgcgctttag cagccccgct   3720
ggcacttggc gctacacaag tggcctctgg cctcgcacac attccacatc caccggtagg   3780
cgccaaccgg ctccgttctt tggtggcccc ttcgcgccac cttctactcc tcccctagtc   3840
aggaagttcc cccccgcccc gcagctcgcg tcgtgcagga cgtgacaaat ggaagtagca   3900
cgtctcacta gtctcgtgca gatggacagc accgctgagc aatggaagcg ggtaggcctt   3960
tggggcagcg gccaatagca gctttgctcc ttcgctttct gggctcagag gctgggaagg   4020
ggtgggtccg gggcgggct caggggcggg ctcaggggcg gggcgggcgc ccgaaggtcc   4080
tccggaggcc cggcattctc gcacgcttca aaagcgcacg tctgccgcgc tgttctcctc   4140
ttcctcatct ccgggccttt ctcgagtccg gattaagatg aacgacgagc agatcctgga   4200
gatggtgctg cagcaccagc agcgccgcca acaggaagcg gagcgcgagg aggaagttgg   4260
ggatgacatg gaagacgacg aagatgatga cggtcttcag atgccgacgc cgcttcatgc   4320
ctatcagcta ctgtgttacg attctttcga acttcatttc gggggatgcg cttgccacgg   4380
gttacctttg catcgtatgg ggttatcggc ttgccacctg gctccttccg atttggccac   4440
ttatgtttgg gccaggttgg aggatgactt gaatgtggca ggggtgtact tcgtggctat   4500
gtgggcgtca ccggggttta gcgatttctc tccagtattt atgcagcgac cgatcgggaa   4560
cgtgtgcggg atgttaattc acgtggacct gcacagcagg ctaccattcc taattgcggt   4620
gtcgcgcttg gggaggcgg gtggcagccc ctgtctgtat atgaggaaaa ttgatgttga   4680
tttggacacg cagcgcgtac atttttatac agaagattgg ttcagtgagt ttgcgaatct   4740
gctgtattac tggcaaatga gcgaatggaa acatttagcg gagcgtatgc aataaagaga   4800
cgtgagactg tataaatggt tcacctgtta acggatccca cgtcactatt gtatactcta   4860
tattatactc tatgttatac tctgtaatcc tactcaataa acgtgtcacg cctgtgaaac   4920
cgtactaagt ctcccgtgtc ttcttatcac catcaggtga catcctcgcc caggctgtca   4980
atcatgccgg tatcgattcc agtagcaccg gccccacgct gacaacccac tcttgcagcg   5040
ttagcagcgc ccctcttaac aagccgaccc ccaccagcgt cgcggttact aacactcctc   5100
tccccggggc atccgctact cccgagctta agattaaggg cgaattcgtt taaacctgca   5160
ggactagtcc ctttagtgag ggttaattct gagcttggcg taatcatggt catagctgtt   5220
```

-continued

```
tcctgtgtga aattgttatc cgctcacaat tccacacaac atacgagccg gaagcataaa   5280

gtgtaaagcc tggggtgcct aatgagtgag ctaactcaca ttaattgcgt tgcgctcact   5340

gcccgctttc cagtcgggaa acctgtcgtg ccagctgcat taatgaatcg gccaacgcgc   5400

ggggagaggc ggtttgcgta ttgggcgc                                      5428
```

IMMORTALIZED AVIAN CELL LINES FOR VIRUS PRODUCTION

CROSS REFERENCE TO RELATED APPLICATIONS

The present application claims priority to European Patent Application No. 03025158.1, filed 3 Nov. 2003, which application is incorporated herein fully by this reference.

The present invention relates to immortalized avian cell lines suitable for production of biologicals or viruses for vaccination. In particular, the cell lines are derived from primary cells which are transformed with at least two viral or cellular genes, one of which causes cell cycle progression whereas the other interferes with innate protective mechanisms of the cell induced by dysregulated replication. The invention moreover relates to the production of said immortalized cell lines and their use for producing biologicals or viruses for vaccination.

BACKGROUND

Embryonated chicken eggs still are one of the main substrates for the production of human vaccines. They are able to support the replication of a wide range of human and animal viruses. This spectrum includes attenuated viruses, i.e. defective viruses that have impaired potential to replicate in human or mammalian cells and can thus be used as vaccines. Attenuation can be generated or maintained by continuous passage in embryonated eggs. Chicken eggs used for human vaccine production must be certified to be free of a defined set of viral and bacterial contamination (specific pathogen-free or SPF). SPF eggs are available from commercial suppliers. The broad applicability and a long international track record has kept this strategy alive despite clear disadvantages:

SPF flocks of chicken and embryonated eggs are expensive and can constitute up to 40% of the cost of vaccines. Furthermore, it is difficult to continually maintain SPF flocks completely free of pathogens which is evidenced by periodic outbreaks of disease in SPF flocks. A vaccine lot cannot be released until the SPF supplier verifies that the parental chickens for the embryonated eggs used to manufacture the vaccine lot were completely free of any disease. This uncertainty adds a significant cost to the preparation of these vaccines. In pandemic situations with sudden need for a particular vaccine (e.g. influenza) the supply of SPF eggs may be severely limited. In addition, the large-scale processes for infecting eggs and maintaining virus growth are time consuming and sometimes inconsistent across different vaccine batches.

With the development of cell culture techniques vaccine manufacturers have replaced embryonated eggs with isolated chicken embryonic fibroblasts. While the use of primary cell cultures improves the safety profile, efficiency and reliability of the manufacturing process, it also further increases costs: chicken fibroblasts are prepared from SPF eggs by mincing embryos to establish and amplify viable cells. Typical for primary animal cells the fibroblasts suffer senescence: the doubling time increases with passaging and eventually all cells die. This process occurs after about 20 passages, much earlier than for rodent or some human cell substrates currently used in vaccine manufacture (such as MRC-5 or WI-38). Fibroblast cultures have to be maintained in the presence of 5-10% fetal calf serum, adding additional risk factors to the manufacturing process. They also require a solid surface for propagation and do not grow in suspension, a preferred state for bioreactor applications. Even with the use of multilayer cell factories this substantially limits scale-up procedures. Due to the limited live span a complete set of safety tests has to be applied for each lot of chicken fibroblasts.

Fibroblasts are the only cell type out of the wide variety of different tissues from a chicken embryo that proliferates well. The predominance of fibroblasts compared to other cell types has in some cases decreased theoretical virus yield because in eggs typically the chorioallantoic membrane, an epithelial cell layer, is the main site for virus amplification.

The discussed problems have contributed to severe influenza vaccine shortages in the last two years (2003 and 2004). To overcome these limitations, a permanent cell line growing in a synthetically defined medium, preferably in suspension or at least on carriers, would be highly desired.

Some of the viruses typically grown in chicken fibroblasts have been adapted to certain cell lines. BHK-21 (baby hamster kidney) cells support the growth of various vaccinia, influenza, and rabies vaccine strains (Drexler, I. et al., J. Gen. Virol. 79(Pt2):347-52 (1998); Gumusderelioglu M. et al., Biotechnol. Appl. Biochem. 33:167-72 (2001); Merten, O. W. et al., Adv. Exp. Med. Biol. 397:141-51 (1996)) and easily grow in large fermenters on carriers under serum-free conditions (Pay, T. W. et al., Dev. Biol. Stand 60:171-4 (1985); Gallegos Gallegos, R. M. et al., Arch. Med. Res. 26:59-63 (1995)). For vaccinia this applies even to the highly attenuated strain Ankara (MVA) which was developed on chicken cells. The BHK-21 cell line is accepted for production of certain vaccines for livestock animals (Lubiniecki, A. S., Bioprocess Technol. 10:495-513 (1990)). However, the BHK-21 line does not meet the safety requirements for human live vaccines. BHK cells have spontaneously formed, are highly tumorigenic and their history is inadequately reported.

According to the FDA, CBER Discussion from May 12 , 2000 on cell substrates the development of "Minimally-Purified Live-Attenuated Viral Vaccines and Virus-Vectored Vaccines" in neoplastic cells derived from naturally occurring tumors from humans and other mammals or from human cells and mammalian cells that have been transformed by unknown mechanisms is discouraged.

As an exception to the rule the VERO cell line (originating from African green monkey) is allowed as a cell substrate for vaccine manufacture based on a proven safety profile and the lack of transformed phenotype for a defined number of passages. The cell line has been used extensively for the manufacture of the polio and smallpox vaccines for clinical use. However, VERO cells require attachment and are amenable only to carrier based processes.

Additionally MDCK cells (a spontaneous cell line from dog kidney epithelium) with a described history have been applied to the manufacture of influenza virus (Tree, J. A. et al., Vaccine 19:3444-50 (2001)).

More recently, triggered by the development of vector based vaccines and gene therapy approaches, new so-called designer cell lines of human origin are intensely discussed and included into the spectrum of potential cell substrates for vaccine production (Vaccines and Related Biological Products advisory committee, session from May 16, 2001). New permanent cell lines were created to provide complementing genes for recombinant viruses that are replication-deficient outside the production system. However, stable introduction of the complementing genes requires prolonged cultivation times, which either exceed the natural limit of passage numbers available to primary cells or the tolerated limit of passage numbers for VERO cells before full transformation occurs.

Designer cell lines are generated in vitro with extensive documentation using characterized genes for transformation.

For example, the complementing genes from the E1 region of adenoviruses by themselves exhibit transforming properties and have allowed establishment of human cell lines, for example PER.C6 (Fallaux, F. J. et al., Hum. Gene Ther. 9:1909-17 (1998)). The application of these cell lines is not limited to the viral vector they are designed for but may be extended to other viruses. For example, influenza virus can be propagated on PER.C6 (Pau, M. G. et al., Vaccine 19:2716-21 (2001)). However, this finding does not apply to all viruses relevant to vaccine development, in particular avian viruses such as Marek's disease, infectious bursal disease, Newcastle disease, turkey herpes, or chicken anemia viruses. While some of these viruses replicate well on mammalian cell lines, virus growth is often poor. For other viruses, replication is poor and limited to particular especially adapted strains.

In addition, with adaptation to a primate-derived cell substrate, receptor binding sites on the virus are likely to change resulting in a modified antigen pattern and thus a general effect on immunogenicity. This genetic adaptation may reverse attenuation for strains which have been developed via passaging in avian cells such as MVA or chicken-adapted measles virus (Escoffier, C., Gerlier, D., J. Virol. 73:5220-4 (1999)), or create new strains replicating more efficiently in human cells compared to their wild type isolates. Such viruses may also obtain a higher pathogenic potential.

For the above reasons vaccine manufacturers are reluctant to switch to mammalian cell lines and a need for immortal avian cell lines has developed.

The investigation of tumor induction in birds by the avian alpharetroviruses provided first molecular insights on cell transformation in general. The retroviral oncogenes are derived from cellular genes with essential regulator domains mutated or deleted. Some of the factors that have been identified in the course of these studies, such as v-myc or v-ras, directly affect components of both retinoblastoma (RB) and p53 pathways. Other proteins, such as v-src or v-erbB, are constitutively activated (hence, dysregulated) signal transducers that mimic impinging extracellular mitogens. The problem with these factors is that they target only one of several pathways required for efficient transformation. The presence of v-src or v-myc predisposes the cell for transformation and requires additional, spontaneous and unpredictable alterations within the cell for full transformation. The risks for the patient posed by cells transformed with one of the retroviral oncogenes therefore is difficult to estimate.

In other cases a single strong tumor antigen (e.g. v-jun) is able to directly cause tumor formation (Hartl, M. et al., Curr. Cancer Drug Targets 3:41-55 (2003)). Many avian viral oncogenes maintain their oncogenic potential in mammalian cells.

Cell lines created by these viruses are not suitable for vaccine manufacturing. A retrovirus carrying an oncogene may get activated and transferred together with the vaccine. Even a tumor antigen not enclosed by viral LTRs may pose a high risk when it is able to transform mammalian cells without the help of complementary antigens. This risk is typically estimated by consideration of the transforming potential, the number of vaccinees, and the amount of cellular nucleic acid transferred with the vaccine virus. This amount is limited by the efficiency of the purification process and currently cannot be reduced to below 10 pg/dose. This criterion is especially stringent for vaccine production where a healthy population often is inoculated at a very young age.

The same arguments apply to transforming DNA viruses such as papillomaviruses and polyomaviruses. These viruses are equiped with aggressive oncogenes: SV40 large T antigen is a multifunctional protein which affects both checkpoint control in G1 of the cell cycle and p53 activity. Therefore, large T readily immortalizes and transforms multiple mammalian tissues of rodent and human origin. With the addition of small T antigen (further enhancing large T action and additionally modulating the AKT3 pathway) it was possible to immortalize avian cells (part of patent application US 2001-0016348). However, even with sophisticated modern purification methods SV40 large-T antigen is considered too aggressive for use in cell lines generated for application in human medicine. In contrast to the above, the genes proposed in this invention affect checkpoint control of the cell cycle and p53 inactivation via separate factors: a required simultaneous transfer event of two distinct factors for transformation dramatically decreases any theoretical risk for the vaccinee.

US patent application 2001-0016348 describes the use of an anti-apoptotic pathway completely unrelated to the present invention. It does not provide a second gene that counters an internal signal for apoptosis due to forced cell cycle progression caused by a first gene. Apoptosis can also be induced by a variety of external simuli, for example lack of growth factors or loss of anchorage. Transmission of this type of pro-apoptotic signal can be inhibited by bcl-2 family genes, the focus of US patent application 2001-0016348.

Whereas 90% of cervix carcinomas carry papillomavirus sequences, C-type adenoviruses (which include types 2 and 5) are considered not to induce tumors in vivo, and adenoviral sequences have not been detected in human tumor tissue.

Alternatively, it has been tried to develop cell lines by continuous passaging of chicken embryonic fibroblasts. Whereas rodent cells appear to undergo spontaneous immortalization quite easily (Curatolo et al., In Vitro 20:597-601 (1984)), avian and primate cells are highly resistant to this approach (Harvey, et al., Genes and Development 5:2375-2385 (1991); Pereira-Smith, J. Cell Physiol. 144:546-9 (1990); Smith et al., Science 273:63-67 (1996)). Somatic cells of avian or primate origin lack telomerase and senescence is caused by the shortening of chromosomal ends (telomeres). Nevertheless, a chicken fibroblast line UMNSAH-DF1 has been developed using this approach (U.S. Pat. Nos. 5,672,485 and 6,207,415). Immortalization by this approach is caused by spontaneous mutations in multiple oncogenes or tumor suppressor genes. This is a rare event which is unlikely to be reproduced especially in cells of other tissue origin. Most importantly, such an approach contradicts the Defined Risk approach as a general rule for human live vaccines proposing detailed knowledge about the immortalizing genes to assess the risk of oncogene transfer. Again, according to the FDA (CBER Discussion from May 12, 2000, on cell substrates) the use of neoplastic cells derived from naturally occurring tumors or cells that have been transformed by unknown mechanisms is discouraged for the development of minimally-purified live-attenuated viral vaccines and virus-vectored vaccines.

The spontaneously developed UMNSAH-DF1 chicken fibroblast line exhibits alterations in E2F and p53 activity (Kim et al., Oncogene 20: 2671-82 (2001)). This is not surprising because enhanced cell cycle activity requires active E2F, and because it is known from mammalian cell studies that high E2F activity induces apoptosis in the presence of active p53. The study characterizes the immortal stage without shedding light on the causative events: mutations in a large number of genes may have caused immortalisation.

A spontaneous transformation process may be enhanced by the use of chemical mutagens (U.S. Pat. No. 5,989,805). The particular cell lines generated using this approach have overcome senescence but maintained a fibroblast like appearance and are non-tumorigenic. Although this represents a significant safety feature, these cells are of low value for large scale fermentation techniques. Furthermore, this chance-based approach also contradicts the Defined Risk guidelines.

Avian cell lines originating from naturally occurring tumors such as a quail fibrosarcoma (WO 97/08307) have also been proposed for biomanufacturing. Again, the Defined Risk guidelines for use in human vaccine production are violated by a method that is based on chance events.

The approaches taken in the studies described above are in sharp contrast to the active introduction of specific groups of immortalising genes according to this invention, which defines the causative agents for immortalisation and allows to assess risk, provides high flexibility with respect to selection of various tissues, and allows to modulate certain features of the resulting cell line.

Despite the fact that chicken eggs and fibroblasts have a considerable track record they are also associated with a very specific risk factor that only recently has come into greater focus: chicken cells release at least two types of retroviral particles, the endogenous avian retrovirus (EAV) and the endogenous avian leukosis virus (ALV-E). The issue is similar to the presence of endogenous retrovirus particles in mouse cells which are used for the manufacture of recombinant proteins (such as NSO). However, in contrast to mouse cells, chicken cells have been shown to contain reverse transcriptase. Due to more efficient detection techniques RT activity has also been detected in chicken cell-derived measles, mumps and yellow fever vaccines (Hussain, A. I. et al., J. Virol. 77:1105-11 (2003); Shahabuddin, M. et al., J. Clin. Microbiol. 39:675-84 (2001)). Whether the presence of reverse transcriptase activity results in transmissible retroviruses remains controversial: a more detailed analysis has shown that CEF (from White Leghorn) contain five loci with integrated EAVs, two of which can express infectious ALV-E whereas the other three are defective (Johnson, J. A., Heneine, W., J. Virol. 75:3605-12 (2001)). Tsang, S. X. et al., J. Virol. 73:5843-51 (1999) also found RT activity and release of viral particles but did not observe any transmission after a careful search for EAV sequences in blood mononuclear cells of children that received mumps vaccine. According to the Weekly Epidemiological Record of the WHO (73) 28 (1998), independent laboratories have investigated the infectivity of the particles for a variety of human and other mammalian cells by extensive co-cultivation and could not detect transmission of RT activity or productive infection. This finding is supported by epidemiological studies that have revealed no association between the use of chicken cell-derived vaccines and incidence of cancers, including those of childhood.

Furthermore, in the mentioned Weekly Epidemiological Record, the WHO stresses the importance of chicken host cells to maintain attenuation of certain vaccine strains. Alternative production processes are not currently available, and this lack of alternatives is an important reason for the acceptance of a known and continous source for a viral contaminant.

However, epidemiological studies superimpose populations and do not investigate chance events or case studies. Epidemiological studies cannot refute theoretical risks, for example: the accepted endogenous RT activity may mask RT activity from unacceptable exogenous contamination, and the endogenous viruses may be mobilized and activated if packaging constructs are introduced into the cells (Ronfort, C. et al., Virology 207:271-5 (1995)).

It was shown, however, that cells from ducks and geese do not contain EAV and ALV related sequence and the Japanese quail is free of reverse transcriptase (Smith, L. M. et al., J. Gen. Vrol. 80(pt1):261-8 (1999); Brudno, I. A. et al., Vopr. Virusol. 97-100 (1980)).

Adenoviruses (AdV) are well characterized, naked (non-enveloped) ubiquitous viruses. For the most common serotypes Ad2 and Ad5 the seroprevalence in the human population approaches 90%. Replication incompetent versions of these viruses are used as gene therapy and vaccine vectors in trials with human patients. Genes from the E1 region of human Adenovirus 5 have been used to transform some specific human cells in vitro (293 and PER.C6 cell lines; Fallaux, F. J. et al., Hum. Gene Ther. 9:1909-17 (1998); Graham, F. L. et al., J. Gen. Virol. 36:59-74 (1977)). The general process is inefficient compared to stronger multifunctional oncogenes such as SV40 large T antigen. Based on the observation that 293 show neuron specific markers and PER.C6 are of neuro-ectodermal origin it was suggested that Ad5 E1-based transformation is limited to neuronal cells (Shaw et al. Faseb J 16(8): 869-71(2002)). Considering the significant species barrier between human and avian cells efficient immortalisation of multiple avian tissues by transfection is even more unexpected.

Mammalian E1 transformed cell lines have been used for the production of live purified adenovirus vectors in clinical trials. With careful monitoring of the amount of contaminating cellular DNA in a vaccine preparation and its size, the transforming genes of Ad5 are not considered a safety hurdle (Vaccines and Related Biological Products advisory committee, session from May 16, 2001).

Adenoviruses replicate in the nucleus of the infected cell. Because quiescent host cells are not permissive for a full viral life cycle adenoviruses have evolved mechanism to force cells into S-phase. To maximize burst size of progeny viruses they have also evolved mechanism to evade apoptosis as a response of the host cell to capsid penetration and viral replication. The genomic region that mediates both cell cycle progression and inhibition of apoptosis is the E1 region.

The E1 region actually consists of two distinct expression cassettes, E1A and E1B, arranged in tandem and each equipped with its own promoter and polyadenylation site. At least three proteins are translated from the E1A primary transcript by alternative splicing. Among others, E1A proteins have been found to disrupt RB/E2F complexes and to interfere with the p300 and CBP transcriptional co-activators. The escape of E2Fs from the RB repressor induces progression of the cell cycle from G1 to S phase, whereas the E1A/p300 complex induces apoptosis via several pathways (Putzer, B. M. et al., Cell Death Differ. 7:177-88 (2000)), including repression of transcription of MdM2, a negative regulator of the key sensor for apoptosis, p53.

As E1A sensitizes cells to TNF-induced apoptosis it is considered an antitumor agent, and it is used in experimental approaches for tumor treatment (Lee, W. P. et al., Cancer Res. 63:6229-36 (2003)).

Furthermore, acting as a transcription modulator it drives cells towards de-differentiation, a feature advantageous to a potential cell substrate.

It was shown by Guilhot et al. (Guilhot, C. et al., Oncogene 8:619-24 (1993)) that retroviral transduction of the 12S protein of E1A from Ad5 can lead to immortalization of quail cells. This is likely the consequence of interaction between the avian RB and E1A. However, the process fails when the gene is introduced by transfection of naked DNA instead of retrovirus infection (pers. observation). We propose that the extremely efficient and stable transduction via retrovirus infection creates a cell pool large enough to harbor individual cells with spontaneous genomic changes that have blocked apoptosis that normally is induced upon RB inactivation. These required but unknown changes increase the risk for vaccinees and the resulting cell line cannot be considered a designer cell line (the result of defined blocks in specific pathways). Moreover, the transforming gene introduced via retroviruses is flanked by inverted terminal repeats and can, therefore, be mobilized. Such an event may even be more pronounced in cell lines that express reverse transcriptase from endogenous retroviruses.

SUMMARY OF THE INVENTION

In view of the above, it is still desirable to develop an avian cell line with convenient growth properties for large scale manufacture, using a defined combination of immortalizing/transforming genes. It is further desirable that none of these genes is able to transform mammalian cells independent of the other genes. Moreover, the action of a single gene should either have no immortalizing/transforming effect or result in apoptosis of cells expressing the respective gene. The risk of joined transfer to a vaccine recipient should further be minimized by positioning the respective genes on separate expression units. Finally, it would be desirable—as the human population is typically exposed to the respective genes—that these genes are not associated with tumor formation in the human population. The cell line to be generated should not release. infectious virus particles from endogenous retroviruses or not exhibit reverse transcriptase activity at all.

It was found that transformation of avian cells with two particular viral and/or cellular genes, one of which affecting the retinoblastoma proteins and the other the p53 protein, provided for a cell line well suited for the production of viruses for vaccination.

The invention thus provides:

(1) an avian cell line immortalized with a combination of viral and/or cellular genes (hereinafter shortly referred to as "gene(s)"), at least one first gene affecting the function of the retinoblastoma protein and at least one second gene affecting the p53 protein or a family member thereof, wherein preferably the first gene overcomes G1 checkpoint control and the second gene prevents apoptosis induced by the first gene;

(2) a method for preparing a cell line as defined in (1) above, which comprises transforming/transfecting a starting cell with the first and second gene;

(3) the use of the cell line as defined in (1) above for the production of biologicals or viruses, preferably for the preparation of a vaccine or for gene therapy; and (4) a method for producing viruses or biologicals using a cell line as defined in (1) above.

SHORT DESCRIPTION OF THE FIGURES

FIG. 1: Schematic sections of the expression plasmids used for enhanced immortalization of primary duck cells (example 2). Polyadenylation signals are omitted for clarity. The alphanumerics at the left are short identifiers for the plasmids. mPGK and hPGK, phosphoglycerate kinase promoters of mouse and human, resp.; ad5, E1-endogenous promoter of Ad5; moCMV, mouse CMV immediate early promoter; tk, herpes simplex virus thymidine kinase promoter; orf 22 and gam1, CELO virus genes; E1A and E1B, adenovirus 5 E1 region genes.

Figure 2:
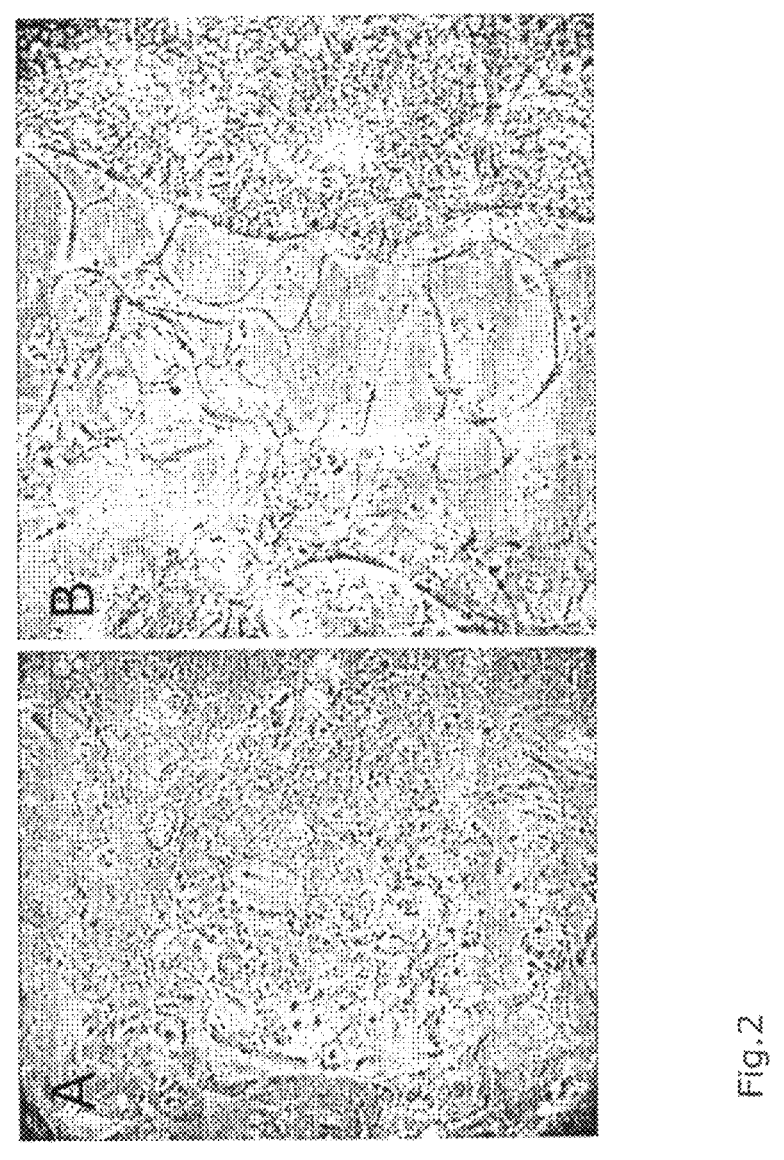

FIG. 2: Phase contrast microscopy pictures as example of focus formation in Ad5-E1 transfected duck embryonal liver cells (plasmid 49E). A, initial magnification 4× to depict a complete focus embedded in senescent primary cells. B, initial magnification 20×: perimeter of a large round focus of small cells arranged in a compact monolayer visible at the right of the panel, primary cells in advanced senescence towards the left.

Figure 3:
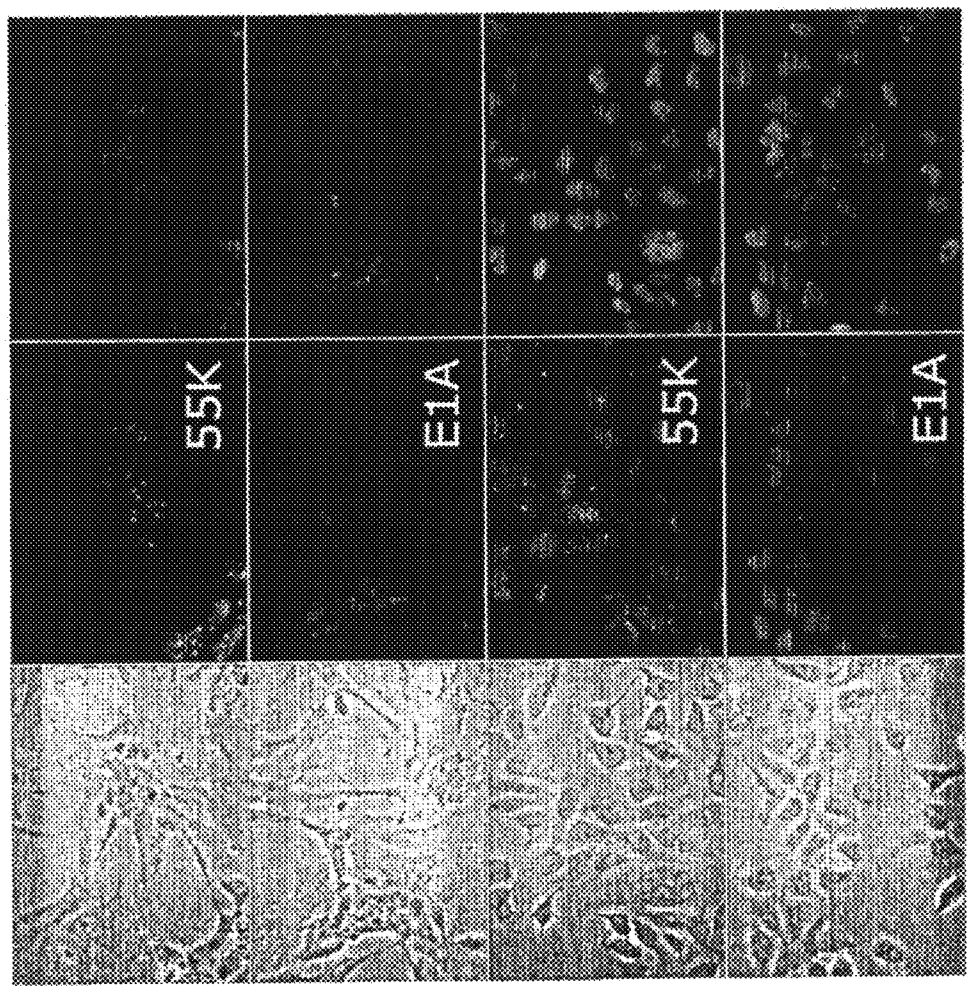

FIG. 3: Immunofluorescence assay for E1A and E1B 55K proteins (example 3). Upper two rows, mix of plasmid 49E-immortalized and primary duck liver cells; bottom two rows, 293 positive control cells. Left column, phase contrast images; middle column, immunostaining of E1A or E1B 55K proteins as indicated in the images; right column, DAPI stain. The E1B 55K protein characteristically localizes to the cytoplasm and accumulates in aggregates to yield an uneven, spotty distribution. E1A is a nuclear protein. Note the compacted nuclei that stain brightly with DAPI in the transformed duck cells.

Figure 4:
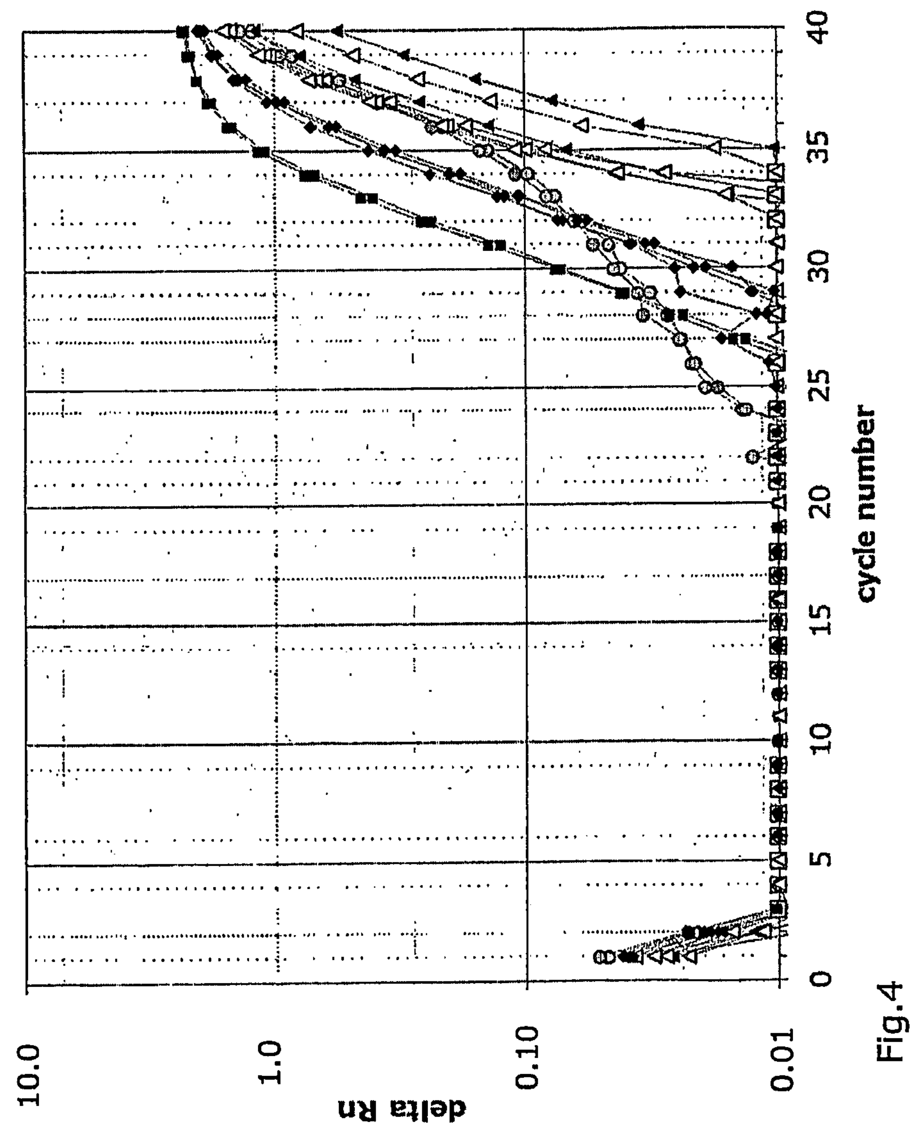

FIG. 4: Q-PERT assay (quantitative PERTassay) on cell supernatant for detection of retroviral activity (example 4). Bold squares, CHO positive control; open squares, water negative control; bold diamonds, chicken embryonic fibroblasts; bold triangles, 293 cell line negative control, grey circles, substrate-only negative control; open triangles, duck liver cells immortalized with plasmid 49E; delta Rn, emission of the reporter dye over starting background fluorescence.

Figure 5:
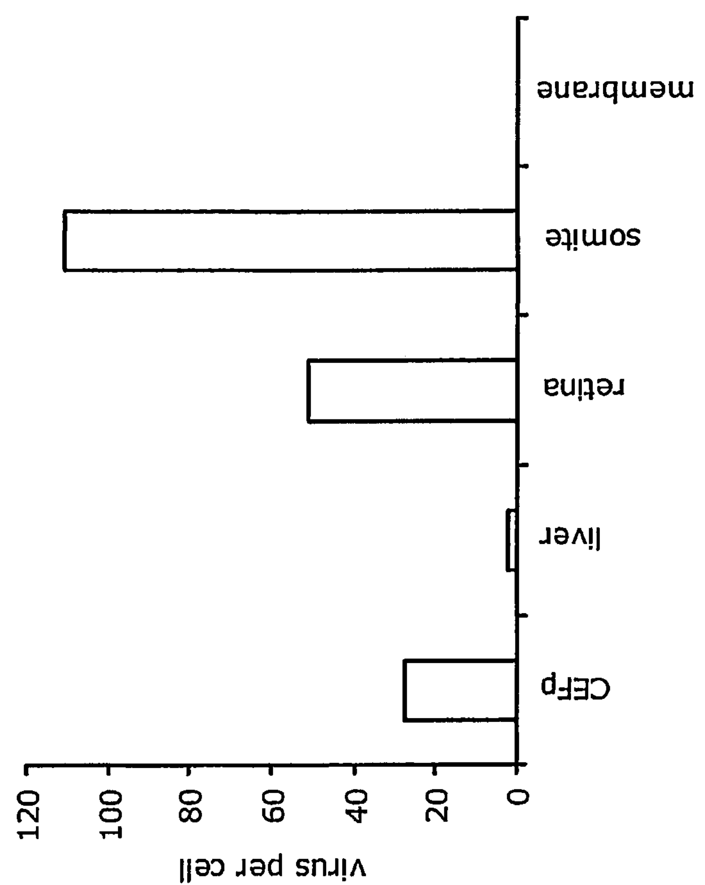

FIG. 5: MVA amplification on some of the described duck cell lines and CEFp (example 5). Infection was performed with an MOI of 0.1. Titration was performed on VERO cells 48 hours after infection (Example 2). CEFp, primary chicken embryonic fibroblasts.

Figure 6:
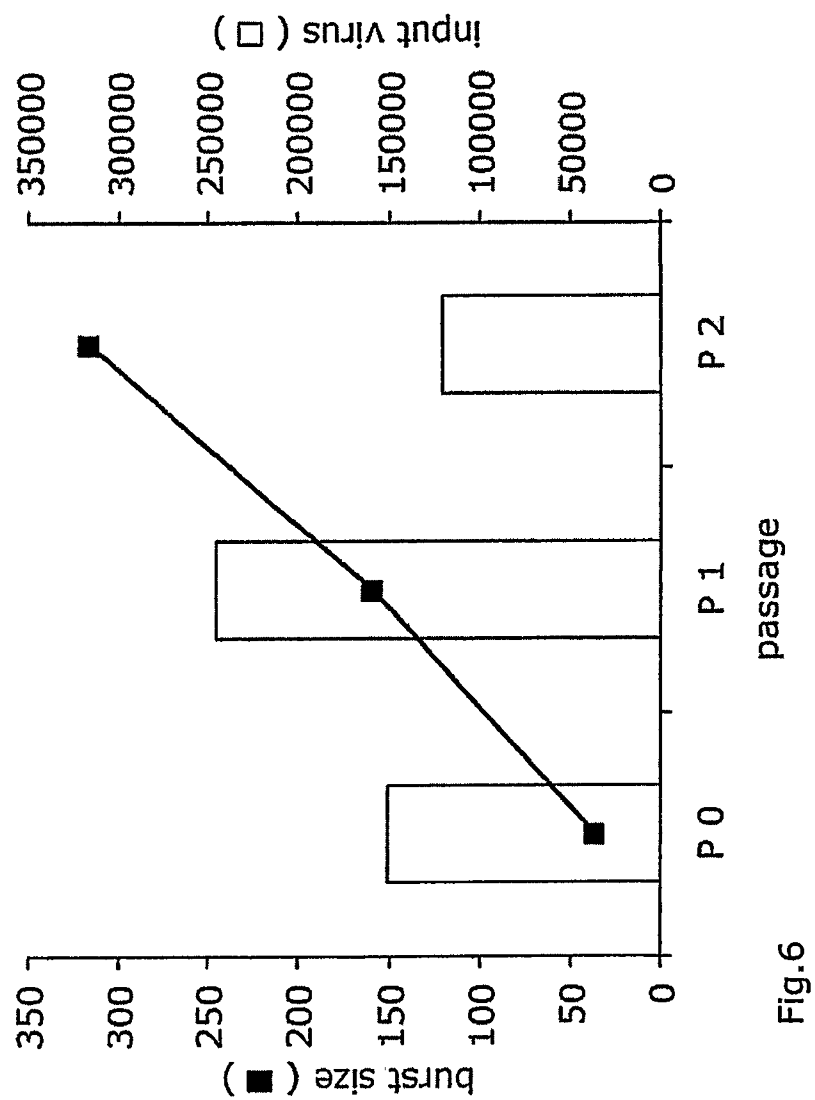

FIG. 6: serial passaging of MVA on duck retina cells immortalized with plasmid 49E (example 5). Bold squares, burst size; bars, input virus adjusted to an MOI of 0.1. Input virus is given as reference to demonstrate that burst size is independent of experimental fluctuations in cell numbers (which in turn define input virus via MOI).

Sequence Listing - Free Text

| SEQ ID NO: | Description - free text |
|---|---|
| 1 | Primer VS182 |
| 2 | Primer VS183 |
| 3 | Primer VS184 |
| 4 | Primer VS185 |
| 5 | Primer VintSA-F |
| 6 | Primer VintSA-R |
| 7 | Plasmid pEFAdBE1A |
| 8 | Plasmid pEFAdSE1BSA |
| 9 | Plasmid 49E |
| 10 | Plasmid 25F |
| 11 | Primer V206 |
| 12 | Primer V207 |
| 13 | Primer V208 |
| 14 | Primer V209 |
| 15 | RT primer |
| 16 | Primer cDNA 1 |
| 17 | Primer cDNA 2 |
| 18 | Plasmid 60E |
| 19 | Plasmid 36E |

DETAILED DESCRIPTION OF THE INVENTION

"Immortalized", "immortalized cells" and "immortalized cell line" according to the present invention relates to a cell or cell line which has been transfected/transformed by certain functional DNA sequences conferring the potential for at least 200 passages, preferably unlimited number of passages, i.e. immortality, to the respective starting cells.

A "gene cassette" of the present invention is to be understood as a DNA sequence comprising a gene affecting the function of the retinoblasoma protein, i.e. which directly or indirectly (e.g. after expression) mediates the disruption of complexes between retinoblastoma proteins and E2F transcription factors, and which in addition comprises a viral gene preventing induction of growth arrest and apoptosis by p53 such as the adenovirus E1B 55K protein of all groups, the E6 protein of papillomaviruses, preferably those of the low-risk human papillomaviruses (HPV) (such as HPV1, HPV6 and HPV11, but not HPV16, HPV18), or a cellular gene preventing growth arrest and apoptosis by p53 such as mdm2.

In more detail, the above gene cassette comprises a "first gene" which in a preferred aspect of (1) directly or indirectly (e.g. via cellular inducers) mediates the disruption of complexes between retinoblastoma proteins and E2F transcription factors. This first gene may be a viral gene such as a mastadenovirus E1A, gam1 and orf22 of CELO or E7 of papillomaviruses, preferably of the low-risk human papillomaviruses (such as HPV1, HPV6 and HPV11, but not HPV16, HPV18), or a cellular gene such as a constitutively active CDK4 or an over-expressed D type cycline. The activity of the first gene mediates cell cycle progression usually at the cost of induction of apoptosis or growth arrest with increased passaging.

A "second gene" is present in above gene cassette to counter this effect of the first gene. It prevents apoptosis or growth arrest and preferably acts by inhibiting transcriptional activation by p53 via augmenting the degradation of p53 or converting p53 from a trans-activator to a repressor of transcription. Preferably the "second gene" is capable of preventing transcriptional activation by p53, including repression of the function of p53 and causing a decrease in stability of p53. The "second gene" may be a viral gene such as the adenovirus E1B 55K protein of all groups, orf22 of CELO, the E6 protein of papillomaviruses, preferably of the low-risk human papillomaviruses (such as HPV1, HPV6 and HPV11, but not HPV16, HPV18), or a cellular gene preventing growth arrest and apoptosis by p53 such as mdm2. Preferably the "second gene" is orf22 of CELO or adenovirus E1B 55k.

This is exactly opposite to the introduction of exogenous active wild type p53 which was associated with the generation of a chicken fibroblast line by an unknown mechanism (U.S. Pat. No. 5,879,924).

"Biologicals" in the context of present invention comprises therapeutic and recombinant proteins, including antibodies, enzymes, hormones, receptors or their ligands and fusions thereof. Prefererred biologicals are recombinant proteins.

One preferred aspect of embodiment (1) is the use of a cell line derived from embryonic or hatched chicken, duck, goose, quail or the like, preferably from chicken or duck. In an especially preferred aspect of (1), additionally this cell line is free of reverse transcriptase activity, derived from immortalization of a primary cell originating from chicken embryos, hatched chicken, duck embryos or hatched ducks, is derived from extraembryonic membrane and/or is cultivated in a chemically defined medium. The medium is preferably free of animal serum.

Another preferred aspect of embodiment (1) is that the cells subjected to immortalization are primary cells including fibroblasts, cells from isolated body segments (somites) or separated individual organs including neuronal, brain, retina, kidney, liver, heart, muscle and extraembryonic tissues and membranes protecting the embryo. Most preferably, the cells are from extraembyonic membranes or retina.

The immortalization leading to the cells of embodiment (1) is preferably effected by non-viral transfection, including, but not limited to, transfection mediated by liposomes, dendrimers or hydroxyapatite ("calcium phosphate") precipitates and electroporation.

Preferably, the first gene in embodiment (1) is a viral gene mediating disruption of complexes between retinoblastoma proteins and E2F transcription factors. This includes, but is not limited to, an adenovirus E1A gene from mastadenoviruses (preferably from mastadenoviruses of group C), an E7 protein of papillomaviruses, preferably from low-risk human papilloma virus (HPV) (such as HPV1, HPV6 and HPV11, but not HPV16, HPV18), an orf 22 gene of avian adenoviruses and/or E43 open reading frames from ovine attadenovirus. Alternatively, the first gene of embodiment (1) is a cellular gene mediating disruption of complexes between retinoblastoma proteins and E2F transcription factors. This includes, but is not limited to, cyclin D1, cyclin D2, cyclin D3 and/or a mutated CDK4 not susceptible to inactivation by p16INK4a.

The second gene of embodiment (1) is preferably a viral gene coding for a protein preventing induction of growth arrest and apoptosis by p53. This includes, but is not limited to, genes coding for the adenovirus E1B55K protein of all groups, GAM-1 of CELO, the E6 protein of papillomaviruses, preferably those of the low-risk HPV (such as HPV1, HPV6 and HPV11, but not HPV16, HPV18). Most preferred are genes coding for the adenovirus E1B55K protein and GAM-1 of CELO. Alternatively, the second gene encodes a cellular protein preventing growth arrest and apoptosis by p53 such as mdm2.

The first gene and second gene of embodiment (1) are preferably either separated spatially by heterologous sequences or located on different nucleic acid segments or plasmids.

In an especially preferred aspect of embodiment (1) the first gene is the E1A and the second gene is the E1B region of an adenovirus from the genus Mastadenovirus, preferably from adenovirus 5. Most preferably said E1A regions have the sequence of bp 1193 to 2309, preferably bp 1239 to 2309, of SEQ ID NO:7 or the sequence complementary to bp 4230 to 3113 of SEQ ID NO:9. Furthermore most preferably said E1B regions have the sequence of bp 1145 to 3007, preferably bp 1197 to 2810, of SEQ ID NO:8 or the sequence complementary to bp 2345 to 550 of SEQ ID NO:9.

In a further especially preferred aspect of embodiment (1) the first gene is orf22 and the second gene is GAM-1 from an adenovirus, preferably from the genus aviadenovirus CELO, which preferably have the sequence represented by the sequence complementary to bp 1252 to 635 of SEQ ID NO:10, and the sequence complementary to bp 3138 to 2290 of SEQ ID NO:10.

In even a further especially preferred aspect of embodiment (1) and (2) the plasmids 36E (SEQ ID NO:19), 37E (FIG. 1), 49E (SEQ ID NO:9), 25F (SEQ ID NO:10) or 60E (SEQ ID NO:18) are used for immortalization of the cells.

Furthermore, combinations of nucleic acids encoding E1A and/or E1B with GAM-1 and/or Orf22 as defined above are preferred aspects of embodiment (1).

The cell line according to embodiment (1) may additionally carry non-natural functional sequences including, but not limited to, transgenes such as genes complementing deficient viruses (e.g. EBNA1, etc.), promoters (e.g. PGK-, EF1.alpha-, CMV-promoter, E1-promoters of Ad5, tk-promoter etc.), enhancers (e.g. RSV-LTR), selection markers such as neomycin-resistance, puromycin-resistance, etc. In one preferred aspect the first and second gene are under the control of separate promoters selected independently from PGK-, CMV-, E1- and tk-promoters.

The cell line according to embodiment (1) is in one preferred aspect furthermore suitable for production of biologicals or viruses including vaccine strains (Marek's disease, infectious bursal disease, Newcastle disease, turkey herpes, chicken anemia, influenza, vaccinia (MVA), rubella, rabies viruses, etc.) and recombinant viral vectors (e.g. recombinant MVA or alphaviruses). Most preferred viruses for vaccination are MVA and influenza viruses. The most preferred recombinant viral vector is MVA.

In one aspect of embodiment (1) the cell line is cell line 12A07-A10 (DSM ACC2695) derived from immortalization of duck extraembryonal membrane cells with plasmid 49E (example 2).

Furthermore preferred is the generation of the cell lines according to embodiment (1) under cGMP conditions which renders them suitable for pharmaceutical application.

The method of embodiment (2) preferably comprises non-viral transfection of the starting cell such as listed above. Most preferred is liposomal transfection, especially transfection by the Effectene reagent.

A preferred use according to embodiment (3) is the use for the preparation of a vaccine or for gene therapy. A viral vaccine strain or gene therapy vector is brought into contact with cells of a cell line according to embodiment (1) so that infection occurs and the virus is amplified by said cells. Continued passaging of virus (repeated cycles of infection and harvest of virus on said cells) will lead to attenuation or adaptation of virus to this particular host cell line. Thus, a viral vector or vaccine strain with lesser virulence for the intended vaccinee (which is not duck, preferably not avian) is generated. Attenuated viruses allow the immune system of the vaccinee to launch a response that is more protective than vaccination with fully inactivated particles, and that is less severe than infection with a wildtype (natural) pathogen. The preferred viruses for this embodiment are measles and rabies viruses.

The method for producing viruses according to embodiment (4) preferably comprises the contacting of said viruses with a cell line according to embodiment (1) and/or the cultivation of said viruses on said cell line. Especially, this method can be used for producing a pox virus, preferably strain MVA, in a duck cell line, preferably a cell line originating from duck somites or duck neuronal tissue, even more preferred from duck retina. Especially duck retina and somite-derived cells obtained by transfection of Ad5-E1 region under cGMP conditions stably support amplification of MVA with an efficiency comparable to or better than primary chicken embryonic fibroblasts (Example 5).

The method for producing biologicals, especially recombinant proteins, according to embodiment (4) comprises the introduction of a gene coding for a recombinant protein, operably linked to a promoter into a cell line according to embodiment (1), cultivating said modified cell line and harvesting the recombinant protein.

The method of embodiment (4) is used preferably for the production of viruses and biologicals usable for vaccination or gene therapy.

Historically, chicken eggs and the respective cells (chicken fibroblasts) are the dominating substrate for the manufacturing of vaccines. For pharmaceutical purposes chicken are available from pathogen-controlled environments with an extensive monitoring system. A large body of literature suggests chicken eggs as the primary target for cell line development. Therefore, chicken cells are one preferred source for starting cells of the invention. However, chicken-derived cells and cell lines will be most likely RT positive. Literature data suggest a low risk for release of infectious virus. However, the absence of transmissible virus will have to be monitored for any cell line to be used in manufacturing. Indeed, most of the avian cell lines established so far are originating from chicken (U.S. Pat. No. 5,830,723, U.S. Pat. No. 5,879,924). Although it was possible to breed a chicken lineage (line 0) free of avian leucosis virus, endogenous avian retroviruses (EAV-HP) (Boyce-Jacino et al., J. Virol 66(8):4919-29 (1992)) are present in chicken cells including line 0. EAVs provide an active reverse transcriptase, but expression levels vary substantially. Therefore, even primary chicken cells and cell lines such as DF1 that tested RT negative in less sensitive assays (Crittenden et al., Virology 57(1):128-38 (1974)) presumably will test positive in modern real time PCR approaches and may harbor retroviruses that are activated under certain growth conditions.

Alternatively preferred avian species of this invention for cell line development are those which do not contain endogenous retroviruses or express reverse transcriptase (RT). This includes ducks, which are suitable for two additional reasons: Duck eggs are also available from pathogen free monitored stocks and ducks are, in contrast to geese, less likely to develop spontaneous tumors. While it is known that many of the relevant vaccine strains replicate well in duck (embryonal) cells as they do in chicken (embryonal) cells (e.g. Marek's disease virus (Witter, R. L., Avian Dis. 46:925-37 (2002)) or rubella (Rocchi, G., Salvadori, A., Nuovi Ann. Ig Microbiol. 21:336-40 (1970))), this remains to be shown for virus strains of primary interest. For other vaccines such data is not available.

To our knowledge it is a novel and unexpected finding of this invention that the highly attenuated pox virus strain MVA (modified vaccinia Ankara) replicates in duck cell lines at similar or higher efficiencies than in commonly used primary chicken embryonic fibroblasts. One intention of the inventors was to provide a safe and robust alternative to primary cells for amplification of viruses that require an avian host, or vaccine strains where a non-mammalian host is preferred. An important virus for which convenient host cells are not available is MVA (modified vaccinia virus Ankara). MVA is a highly attenuated pox virus and an extremely promising tool for therapeutic and protective vaccine applications. MVA will serve as a model virus for characterization of duck cells but should not be taken as an exclusive example: the described experiments can also be performed with a range of other viruses, whether pathogens or therapeutic vectors, such as measles, rubella, rabies, or influenza viruses.

Fibroblasts have been selected as the preferred cell type mainly for historic and practical reasons. Fibroblasts are the fastest growing primary cells from mammalian as well as avian species. When a cell suspension from whole chicken embryos is brought into culture, this is not the only but the predominant cell type. However, fibroblasts grow strongly adherent and loose this feature only after complete (tumorigenic) transformation. This process requires the presence of strong transforming genes such as v-ras interfering with signal transduction pathways. Early senescence of fibroblast cultures is in part caused by the total absence of telomerase activity in birds and man (Forsyth, N. R. et al., Differentiation 69 (4-5):188-97 (2002)).

Human primary fibroblasts are refractory to transformation with the E1 genes of adenovirus type 5 which do not directly interfere with these pathways (personal observation). Efficient immortalization and growth in suspension culture has a higher chance to succeed for epithelial and neuronal cells. Moreover, epithelia instead of fibroblasts seem to be the primary site for virus replication inside the bird egg. Interestingly, in contrast to the human situation, bird kidney does express telomerase throughout life which makes bird kidney cells a good target for immortalization. Taken together, bird epithelial cells including kidney epithelium and neuronal cells are considered the most promising targets to develop a cell line of the required features.

It is therefore only for the ease with which fibroblasts are obtained that avian cell line development has almost exclusively focused on these cells (Cowen, B. S., Braune, M. O., Avian Dis 32(2):282-97 (1988); U.S. Pat. No. 5,830,723). In some cases whole embryos have been used (US 2001-0016348).

Viruses do not only exhibit species but also organ and tissue specificity based on receptor distribution and cellular factors supporting replication. Therefore, in contrast to the typical approach, a preferred way to perform present invention is the separation of organs prior to cultivation to obtain a most preferred host cell.

For influenza virus, whose vaccine-adequate production is a major application for the cell lines of present invention, the typical site of replication is not the embryo itself but extraembyonic membranes. Therefore, a specific aim was to also develop cell lines from extraembryonic material, including protective membranes of the embryo. Some tissue specific primary cultures including those of the extraembryonic membranes have very short survival times compared to fibroblasts. This further highlights the need for designed immortalization to obtain optimized host cells. Successful immortalisation of multiple tissues in a limited time window requires the specific combination of genes used within present invention.

It was not known which of the avian tissues has the highest replicative potential for pox viruses such as MVA or Canarypox. The typical manufacturing process for MVA involves a mixture of cells from an embryo excluding the head which is removed prior to disintegration. It is therefore completely unexpected that a cell line of neuronal origin, developed from the retina, has such a high capacitiy for MVA replication whereas other tissues have not.

The same tissue specificity applies to protein production. The transcriptional capacity is dependent on the available set of transcription factors and even strong ubiquitous viral and cellular promoters exhibit variable strength in different tissues. Moreover, yields of secreted protein strongly depend on the capability of a particular cell type to fold and process (e.g. glycosylate) the protein properly.

The mechanisms leading to immortalization and transformation of primary cells have been well described (Hahn, W. C. et al., Nature 400:464-8 (1999)). Required elements interfere with (1) control of cell cycle progression, (2) programmed cell death induced by the deregulated cell cycle, (3) growth factor signal transduction and for human and avian cells (4) shortening of the telomeres, the linear termini of the chromosomes. A large number of factors are known that can drive primary cells to an immortalized and transformed phenotype but immortalization comes at the cost of inhibiting cellular checkpoints that are responsible to minimize tumor formation in the host. It is therefore desired to select transforming factors that can effect experimental generation of a cell line but pose a minimal risk of tumor induction in the recipients of biologicals derived from the designer cells. This requirement needs to be balanced with the strength of the transforming factors: they should be strong enough to cause transformation without the need for accumulation of additional spontaneous mutations; that is, the molecular pathway leading to the resulting cell line should be known completely (categories I and II according to the FDA CBER Office of Vaccine's presentations at the May 2000 Advisory Committee). It is furthermore desired to select a synergistic combination of factors that individually cannot transform primary cells so that a concurrent transfer of genetic material is required which further minimizes the risk of inadvertent transformation in vaccinees or patients. Finally, it is desired that the transforming factor elicits an immune response in the recipient of biologicals so that immune tumor surveillance is activated in the unlikely event of tumor formation due to product application. The last criterion can be realized if non-cellular but foreign, for example viral, transforming proteins are utilized.

It was now found that the E1 region from human adenovirus 5 (Ad5) is ideally suited to transform avian cells so that the resulting designer cell complies with all of the above criteria.

The E1B region encodes two open reading frames on a bicistronic mRNA, the 21K and 55K proteins. The 55K protein binds to p53 and thus turns the pro-apoptotic transcriptional activator into a repressor. The 21K protein complements this anti-apoptotic activity by binding to Bax, thus maintaining integrity of the mitochondrial membrane and preventing the release of cytochrome C. This protein is essential to drive adherent cells towards substrate independent growth and hence is essential to a fermentation process in suspension.

It has not been shown before whether human adenovirus E1B 55K can affect the avian homologues of p53. Furthermore, the avian adenoviruses are not equipped with genes resembling E1B so that inference also was not possible. Contrary to all expectations, the inventors have found that E1B can provide the essential functions to allow immortalization by E1A.

A novel and crucial factor for the here described achievement was removal of E1B from its weak natural context and placement under control of a strong, recombinant promoter. This novel modification and combination allowed efficient immortalization of multiple tissues from duck and chicken by transfection instead of retroviral transduction.

Although the underlying mechanism for transformation by E1 is complex one hallmark is a most desirable feature: E1A is a strong inducer of cell proliferation and apoptosis whereas E1B proteins efficiently interfere with apoptosis but cannot release restriction on cell cycle control.

Hence, not a single factor but the continuous presence of E1A and E1B proteins are required to sustain the experimentally induced transformed phenotype.

Since the description of v-src in the 1970s (Brugge, J. S., Erikson, R. L., Nature 269:346-8 (1977)) a panoply of transforming factors have been discovered and characterized. Indeed, it was the study of induction of tumors in birds by alpharetroviruses that provided first molecular insights (Martin, G. S., Nature 227:1021-3 (1970)). The retroviral oncogenes are derived from cellular genes with essential regulator domains mutated or deleted. Some of the factors that have been identified in the course of these studies, such as v-myc or v-ras, directly affect components of the RB and p53 pathways. Other proteins, such as v-src or v-erbB, are constitutively activated (hence, dysregulated) signal transducers that mimic impinging extracellular mitogens. The problem with these factors is that they target only one of several pathways required for efficient transformation. The presence of v-src or v-myc predisposes the cell for transformation and requires additional, spontaneous and unpredictable alterations within the cell for full transformation. The risks for the patient posed by cells transformed with one of the retroviral oncogenes therefore is difficult to estimate.

Other DNA viruses such as papillomaviruses and polyomaviruses are also known to transform cells in vitro. However, the selected transgenes should not be too aggressive to minimize the risk of tumor induction in the recipients of biologicals via inadvertently transferred cellular DNA. This criterion is especially stringent for vaccine production where a healthy population often is inoculated at a very young age. Even with sophisticated modern purification methods polyomavirus Large-T antigen is considered too aggressive for use in cell lines generated for application in human medicine. Whereas 90% of cervix carcinomas carry papillomavirus sequences (Munoz, N. et al., N. Engl., J. Med. 34816):518-27 (2003)) C-type adenoviruses (which include type 2 and type 5) are not considered to induce tumors in vivo and adenoviral have not been detected in human tumor tissue.

Based on the complementary features of the transforming genes shown above, it was found that a combination of genes each interfering with single pathways in the cell cycle and apoptosis is necessary to obtain a genetically stable cell line growing in suspension.

It was shown that the complete E1 region of adenovirus 5 can fulfill these requirements. Whereas it was shown, that the 12S protein of E1A from Ad5 can interact with avian RB (Guilhot, C. et al., Oncogene 8:619-24 (1993)) the functional activity of 55K and 21K proteins in avian cells is demonstrated for the first time in present invention. It is not surprising that some clones of quail cells expressing the 12S protein of E1A exhibit transformed features (Guilhot, C. et al., Oncogene 8:619-24 (1993)). The extremely efficient and stable transduction via retrovirus infection creates a large enough cell pool to allow individual cells to overcome the cell cycle block or induction of apoptosis by spontaneous genomic changes. These required but unknown changes increase the medicinal risk and the resulting cell line can not be considered a designer cell line, which should be based on known genes. Moreover, transfection techniques are not sufficient to create the large clone pool required for natural selection. Instead retrovirus transduction was required. The transforming gene introduced via this approach will be flanked by ITRs and can, therefore, be mobilized, even more in a cell line expressing reverse transcriptase.

Recently, an avian adenovirus, termed fowl adenovirus type 1 strain CELO (for chick embryo lethal orphan), has been described in greater detail (Chiocca, S. et al., J. Virol. 70:2939-49 (1996)). Large, central genomic stretches of CELO are homologous to Ad5 but differ in important aspects—among others, CELO is not equipped with an E1-homologous region. Furthermore, CELO cannot complement Ad5 mutagenized in E1A and, conversely, Ad5 E1 proteins cannot trans-activate transcription of delayed-early CELO genes (Li, P. et al., J. Gen. Virol. 65(Pt 10):1817-25 (1984)). And yet, CELO is capable to transform hamster cells in vitro (May, J. T. et al., Virology 68:483-9 (1975)). Genes interfering with cell cycle and apoptosis, orf22 and GAM-1, have been identified in the CELO virus (Lehrmann, H., Cotton, M., J. Virol. 73:6517-25 (1999)). Orf22 encodes a protein that interact with RB, and GAM-1 interferes with apoptosis in a fashion similar to the prototypical 21K protein (Chiocca, S. et al., J. Virol. 71:3168-77 (1997)).

It was now found that the genes orf22 and GAM-1 from CELO virus are suitable substitutes for E1A and E1B. The spectrum of available transgenes for transformation of avian cells is therewith expanded. These proteins have not been used previously to transform avian cells.

Furthermore, one of the viral genes may be replaced by a cellular gene. Candidates for such replacement are E2F family members or D group cyclins for the E1A region of adenovirus and mdm2 for the E1B region.

The following cell lines were deposited at the DMSZ, Deutsche Sammlung von Mikroorganismen und Zellkulturen GmbH, Mascheroder Weg 1b, 38124 Braunschweig, Germany:

1. PBG04 as DSM ACC2577, deposited on Sep. 18, 2002;
2. 12A07-A10 as DSM ACC2695, deposited on Oct. 20, 2004.

The invention will be explained in more detail by reference to the following Examples, which are, however, not to be construed as to limit the invention.

EXAMPLES

Example 1

Immortalization of Primary Duck Cells with Adenovirus 5 E1A,B

The adenovirus sequences for E1A and E1B were amplified from the culture of passage 8 of the first generation (E1 deleted) adenovirus Admuc grown in HEK 293 which was heavily contaminated with wild type virus using provestart polymerase (Qiagen).

The following primers were used:

```
VS182    ACTCGAGCTGACGTGTAGTGTATT    (SEQ ID NO:1)

VS183    CACACGCAATCACAGGTT          (SEQ ID NO:2)
```

to amplify the E1 A region and

```
VS184    ACTCGAGTCATGGAGGCTTGGGAGT   (SEQ ID NO:3)

VS185    ACACATTTCAGTACCTCA          (SEQ ID NO:4)
```

to amplify the E1 B region. Both fragments were first cloned into pPCR4blunttopo (Invitrogene).

The E1B construct misses the splice acceptor from the E1B message. It was therefore replaced by a synthetic one amplified using primers from the leader intron of a human immunoglobulin heavy chain. As template, the genomic DNA from PBG04 (DMSZ ACC2577), a murine-human heterohybridoma was used.

Primers:

```
VintSA-F  AAGGTACCCTCCCTAGTCCCAGTGA  (SEQ ID NO:5)

VintSA-R  CAATGTACAGAGTGGGCTCCTGTGG  (SEQ ID NO:6)
```

This splice acceptor was directly cloned into pEFmyc, containing aEF1 alpha promoter and the myc leader peptide to create fusion proteins. The E1A region was removed from ptopoE1A using EcoR I and Xho I sites and cloned into pEFmyc directly, removing the myc leader sequence and fusing the E1A to the bovine growth hormone poly A. The E1B region was again removed with EcoR I and Xho I restriction enzymes and cloned into pEFmycSA containing the heterologous splice acceptor site. The resulting plasmids were named pEFAd5E1A (SEQ ID NO:7) and pEFAd5E1BSA (SEQ ID NO:8).

Embryonated duck eggs were incubated at 37° C., 60% air humidity, for 12 days (older embryos yielded more cells but also contained a higher number of contaminating, differentiated fibroblasts). The shell was sterilized with 70% isopropanol, opened at the large end, and the embryo was removed aseptically to a sterile petri dish. The fetal brain and kidneys were removed, transferred to separate petri dishes filled with trypsin/EDTA and minced. After a brief incubation a suspension thereof was mixed with an excess of F12 medium (Gibco/Invitrogen) supplemented with 10% fetal calf serum (Biochrom) and 2% Ultroser G (Ciphergen). This suspension was transferred into a petri dish and cultivation was performed at 37° C. (which is lower than the 41.6° C. physiological temperature of chicken) and 5% $CO_2$. The culture medium with non-adherent debris was replaced the following day and cultivation continued until at least $5\times10^5$ cells per 3.5 cm dishes were available for transfection of plasmids pEFAd5E1A and pEFAd5E1BSA.

Initial experiments comparing liposomal (Effectene; Qiagen) and dendromeric (Polyfect; Qiagen) transfection reagents suggested best efficiencies with Effectene. Transfection there was performed using the Effectene reagent; briefly: 2 μg of plasmid DNA was diluted in 200 μl EC Buffer containing 16 μl Enhancer. After an incubation time of 5 min, 16 μl Effectene was added. After an incubation time of 10 min, supernatant was removed from the culture in 3.5 cm dishes and replaced with 1 ml fresh medium containing the transfection mix. After an incubation time of 2 hours at 37° C. and 5% $CO_2$, additional 2.5 ml fresh medium was added to the culture.

The transfected cells were allowed to reach confluency, trypsinated, resuspended in FCS/Ultroser G-supplemented F12 medium, and re-seeded into two 6 well plates (corresponding to a 12-fold expansion). After 5 and 10 days, the medium was replaced with F12 supplemented only with 5% FCS. The plates were scanned for the appearance of foci of cells with changed morphology (decrease in overall cell size, increased size of nucleus, increased visibility of plasma membranes under phase contrast) and increased confluency.

Approximately 14 days post transfection, once the foci reached a diameter of 1-3 mm the medium was aspirated and the culture washed twice with trypsin/EDTA (Gibco). Trypsin-soaked cloning disks (Sigma) were placed on top of the aspirated foci for 3 min, then transferred into wells of a 24-well plate filled with 500 μl of F12 medium supplemented with 5% FCS.

The cloned, transformed cells were allowed to proliferate until confluency, trypsinized, resuspended in F12 medium supplemented with 5% FCS and transferred into 6-well plates. Once the culture reached confluency in the 6-well plate the cells were transferred to T25 flasks for continuous passaging.

For cryopreservation at defined intervals cells were trypsinized, resuspended in F12 medium containing 5% FCS, collected by centrifugation at 100 g for 10 min, resuspended in F12 medium containing 50% FCS and 10% DMSO (Sigma) to a concentration of approximately $3\times10^6$ cells per ml, and placed in cryovials in an isopropano-based cooling device at −75° C. The cooling device ensures a constant cooling rate of 1° C. per min. After 24 hours the cells were transferred to liquid nitrogen for permanent storage.

Example 2

Improved Preparation of Immortalized Avian Cell Lines a) Preparation of Primary Cells The flock of origin for the duck eggs was certified to be free of *Salmonella enteritidis* and *S. typhimurium; Mycoplasma gallisepticum* and *M. synoviae*; cases of leucosis, reticuloendotheliosis, psittacosis, avian influenza, duck hepatitis, and Derzsy's disease. The animals intentionally were not vaccinated against parvovirus and no cases of parvovirosis were detected. Animals in the flock of origin have been vaccinated against *S. enteritidis* and *S. typhimurium; Pasteurella multicodica*; the metapneumovirus Turkey rhinotracheitis; and the paramyxovirus causing Newcastle disease.

The eggs were allowed to equilibrate without agitation at room temperature and after two days were incubated at 38° C. in a damp chamber, rotated frequently by alternating +45° and −45°.

Duck embryos were sacrificed for isolation of primary cells after one or three weeks of incubation. Eggs were transferred to a cGMP unit (a closed laboratory performing as outlined by the Current Good Manufacturing Practices) and the shell was sterilized by wiping with 70% isopropanol under a laminar flow hood. All subsequent steps were performed in the GMP unit under sterile conditions with defined solutions or media.

Eggs were opened carefully, embryos transfered to a large petri dish and killed immediately by decapitation. Samples from the following organs were removed: brain, retina, liver, esophagus, heart, and extra-embryonic membranes.

In addition, cells from somites were prepared from an 8-day-old embryo.

All samples were rinsed with PBS (phosphate buffered saline; Gibco/Invitrogen, USA), treated with trypsin (Gibco/Invitrogen, USA) for 1 to 10 min, and triturated in DMEM: F12 culture medium (Gibco/Invitrogen, USA) supplemented with 10% FCS (Biochrom AG, Germany) by repeated passaging through an 18G syringe. The homogenized samples were cultivated at 37° C. and 5% $CO_2$. Debris was removed from adherent cells by change of medium the following day.

b) Plasmid Constructions

Expression plasmids for E1A, E1B, Orf22, and Gam1 were constructed by extraction of the relevant target regions from the genomic DNA of adenovirus serotype 5 or chicken embryo lethal orphan (CELO) wildtype virus, respectively, by PCR and insertion into vectors equipped with human or mouse phosphoglycerate kinase (hPGK or mPGK), mouse CMV (moCMV) or tk promoters (FIG. 1).

The adenovirus sequences for E1A and E1B were amplified from wild type virus using ProofStart polymerase (Qiagen, Germany). The following primers were used:

```
VS182    ACTCGAGCTGACGTGTAGTGTATT     (SEQ ID NO:1)
VS183    CACACGCAATCACAGGTT           (SEQ ID NO:2)
```

to amplify the E1 A region and

```
VS184    ACTCGAGTCATGGAGGCTTGGGAGT    (SEQ ID NO:3)
VS185    ACACATTTCAGTACCTCA           (SEQ ID NO:4)
```

to amplify the E1 B region. Both fragments were first cloned into pPCR4-Blunt-TOPO (Invitrogene, USA).

The E1B construct misses the splice acceptor from the E1B message. It was therefore replaced by a synthetic one amplified using primers from the leader intron of a human immunoglobulin heavy chain. As template, the genomic DNA from PBG04 (DMSZ ACC2577), a murine-human hetero-hybridoma was used.

Primers used for amplification:

```
VintSA-F  AAGGTACCCTCCCTAGTCCCAGTGA  (SEQ ID NO:5)
VintSA-R  CAATGTACAGAGTGGGCTCCTGTGG  (SEQ ID NO:6)
```

The genes GAM-1 and ORF-22 were amplified from wild type CELO virus with primers

```
V206
                                        (SEQ ID NO:11)
AAC CTC GAG ACC CCC CTG TAC ATT CTA
and

V207
                                        (SEQ ID NO:12)
GCC GTT AAC TTC AGG GAT TGG TTA CAG,
and

V208
                                        (SEQ ID NO:13)
CAC CTC GAG TCC GGA TTA AGA TGA ACG
and

V209
                                        (SEQ ID NO:14)
CCA GTT AAC AGG TGA ACC ATT TAT ACA G,

respectively.
```

Representative examples for the resulting plasmids are given with plasmid 49E (adenoviral factors under control of human PGK and mouse CMV promoters; SEQ ID NO:9), plasmid 25F (CELO factors under control of mouse and human PGK promoters; SEQ ID NO:10), plasmid 60E (adenoviral factors under control of human PGK and tk promoters; SEQ ID NO:18) and plasmid 36E (CELO factor under control of mouse PGK promoter; SEQ ID NO:19) (see also FIG. 1).

Integrity of the expression plasmids was confirmed by sequencing. The plasmids are not equipped to express resistance factors against antibiotics (such as ampicillin) in eukaryotic cells.

c) Transfection

Primary cultures were transfected with expression plasmids for E1 or Orf22/Gam1 shortly after isolation or after single subcultivation. Depending on the experiment, plasmids were transfected as supercoils or after linearization with the Sca I (New Englands Biolabs, USA) restriction enzyme. Initial experiments comparing liposomal (Effectene; Qiagen, Germany) and dendromeric (Polyfect; Qiagen, Germany) transfection reagents suggested best efficiencies with Effectene. Transfection was performed as follows: 2 μg total DNA was diluted into 200 μl provided EC buffer and mixed with 16 μl provided enhancer. After an incubation for 2-5 min at room temperature 20 μl Effectene reagent was added. After 5-10 min at room temperature this mixture was applied to the cells in a 8 $cm^2$ dish under 1 ml culture medium. After 2-5 hours an additional 1.5 ml culture medium was added. On the following day, the medium was replaced with 2 ml fresh culture medium, and thereafter once per week. Successful transfection was confirmed in parallel experiments with a reporter gene.

The cells were continously passaged in DMEM:F12 medium containing 10% FCS.

Twenty days after transfection changes of morphology in defined subpopulations (foci; FIG. 2) of some cultures were observed; in other cultures foci did not appear or were not able to compete with robust proliferation of the primary cells; again other cultures suffered massive cell death and senescence shortly after transfection.

A large number of independent foci were expanded from plasmid 49E-transfected cultures with cells derived from liver, retina and extra-embryonic membrane. At passage 10, e.g., cell line 12A07-A10 derived from duck extraembryonal membrane cells transformed with plasmid 49E was isolated and deposited at the DSMZ.

Foci were also obtained from plasmid 60E-transfected cultures with cells from retina and somites.

In plasmid 49E, PGK and mouse CMV promoters drive expression of E1A and E1B, respectively. Plasmid 60E (SEQ ID NO:18) also encodes the full Ad5-E1 region but expression of the protective E1B region is driven by tk, i.e. a promoter that is not as strong as the mouse CMV promoter (but stronger than the native E1B promoter). Consistent with the protective effect conferred by E1B far fewer foci in fewer cell samples were obtained with this construct when compared to the results with plasmid 49E.

Formation of foci with both primary cell appearance and transformed phenotype was also observed in cultures of liver transfected with CELO plasmids 36E (SEQ ID NO:19) and 25F (SEQ ID NO:10).

Cultures with foci were expanded by treatment with trypsin for 2-3 min and resuspension in DMEM:F12 medium for transfer to fresh culture vessels.

For cryopreservation at regular intervals cells were removed with trypsin, resuspended in DMEM:F12 medium containing 10% FCS, collected by centrifugation at 200×g for 10 min, resuspended in DMEM:F12 medium containing 50% FCS and 10% DMSO (Sigma, USA) to a concentration of approximately $3\times10^6$ cells per ml, and cooled with a rate of 1° C. per min to −80° C. After 24 hours, the cells were transferred to liquid nitrogen for permanent storage.

Example 3

Immunofluorescence Assay for Stable Transfection

Cultures of potentially immortalized cells were seeded on glass slides and allowed to proliferate for several days before fixation with ice-cold methanol for 10 min. The fixed cells were incubated with antibodies against E1A and E1B 55K proteins, secondary antibodies, and fluorescent dye specific against the latter according to standard immunofluorescene methods (Becton Dickinson, UK, #554155 antibody against E1A, diluted 1:30; Oncogene, USA, #DP08-100UG antibody against E1B 55K, diluted 1:30; secondary antibody directed against mouse or rat, respectively, and conjugated to biotin, both from Jackson Immuno Research, USA, diluted 1:80; visualization with Jackson Immuno Research, USA, #016-070-084 streptavidin-Texas Red conjugate, diluted 1:100). Primary cells still abundant in early, not yet fully established immortalized cell lines and readily distinguishable by morphology provided a convenient internal negative control for antibody specificity. 293 cells (human embryonic kidney cells) that stably express the Ad5 E1-region served as positive control. DAPI (4',6-diamidino-2-phenylindol; Sigma, USA) to 1 μg/ml was added in the final incubation step to stain the nuclei of the cells for orientation purposes.

A strong signal for E1A and 55K was observed only in cells that underwent characteristic changes in morphology confirming successful immortalization by the transfected plasmids (FIG. 3). Furthermore, spontaneous transformation, a formal possibility, was not observed as all cells with altered phenotype were E1-positive. None of the cells with primary phenotype expressed E1-proteins. Although possible in transfections of supercoils where the linearization of plasmid in the process of integration occurs at random positions none of the examined foci exhibited E1A expression in absence of E1B expression, further emphasizing the requirement for dual pathway disruption for immortalization.

Example 4

Assay for Endogenous and Exogenous Retroviruses

A common problem encountered when vaccines are produced in primary chicken fibroblasts is contamination with exogenous or endogenous retroviruses. The diversity of the retrovirus family is too complex to predict whether a given species is a carrier for retroviruses. Reports from the literature therefore usually are limited to a subset of the retrovirus family, for example EAV-HP/ALV subgroup J (Smith, L. M. et al., J. Gen. Virol. 80(pt1):261-8 (1999)), and then only to a subset of avian species.

A reliable confirmation of contamination with retroviruses therefore should focus on a common motif present in these viruses. Sequence diversity precludes nucleic acid-based detection methods. However, common to all retroviruses is the presence of the reverse transcriptase enzyme. The supernatant of expanded foci from duck liver cells immortalized with plasmid 49E was therefore assayed by quantitative probe-based product enhanced PCR for reverse transcriptase (Q-PERT) and compared to several controls, inter alia CHO as positive control and 293 cells as negative control (see below and FIG. 4), to detect both endogenous retroviral activity or contamination with free retroviruses. The assay is a modification from the literature (Lovatt, A. et al., J. Virol. Methods 82(2): 185-200 (1999)). Briefly: retroviruses were enriched from culture supernatant by ultracentrifugation with 100000×g through a barrier of 20% sucrose in PBS to remove cellular debris. Virions (if present) were resuspended into lysis buffer (50 mM Tris pH 7.8, 80 mM KCl, 2.5 mM DTT, 0.75 mM EDTA, 0.5% Triton X-100) and mixed with substrate buffer (10 mM each of dATP, dCTP, dGTP, and dTTP; 15 μM specific primer [GCC TTT GAG AGT TAC TCT TTG; SEQ ID NO:15]; and 0.5 mg/ml fragmented herring sperm DNA [Promega Corp, #D1811]) containing a model RNA (5 μg/ml Brome Mosaic Virus RNA [Promega Corp, USA, #D1541]) that is reverse transcribed if RT activity is present in the sample. cDNA from the model RNA is amplified by PCR with primers (AAA CAC TGT ACG GCA CCC GCA TT; SEQ ID NO:16) and (GCC TTT GAG AGT TAC TCT TTG; SEQ ID NO: 17) and detected via SYBR green fluorescence in an AB 7000 Sequence Detection System using the QPCR SYBR Green ROX Mix #AB-1163 from Abgene, UK, according to the instructions of the manufacturer.

FIG. 4 demonstrates strong RT activity in CHO cells as expected from reports in the literature (for example, Anderson, K. P. et al., Virology 181(1): 305-311 (1991)). With these cells as positive control and human 293 cells free of retroviral activity as negative control a bracket is defined that allows interpretation of unknown RT activity in the supernatant of cell cultures (FIG. 4, bold squares and bold triangles).

We found moderate RT-activity in chicken embryo fibroblasts (FIG. 4, bold diamond symbols).

The signal for RT activity in the duck cell supernatant was congruent with the signal for RT activity in 293 cells, and both again congruent with a control representing the detection limit for our assay consisting of model RNA not incubated with RT (FIG. 4, compare curves with open and bold triangles and grey circles). Equivalent levels of signal intensity (delta Rn) were separated by at least two cycle numbers between samples from CHO cells and chicken embryo fibroblasts (that for these experiments are derived from a source known to be only weakly RT-positive) and by at least four cycle numbers between samples from CHO cells and the 293 negative control and the duck cell culture. Thus, contrary to chicken cells the described duck cells do not exhibit RT activity and thus fulfill an essential attribute for suitability in pharmaceutical applications.

Example 5

Modified Vaccinia Virus Ankara (MVA)

Suitability of the expanded foci as substrate for amplification of MVA was determined for liver, retina, somites and extra-embryonic membrane lines. Table 1 and FIG. 5 show results obtained by infection of the cell lines with an inoculum prepared from a large scale preparation of MVA (ATCC #VR-1508) on CEFp, primary chicken embryonic fibroblasts. The data in the table obtained by infection with an MOI (multiplicity of infection or number of infectious particles per host cell) of 0.1 demonstrates that viral output of retina and somite cells (in plaque forming units per ml) are comparable to or even exceed the output obtained with CEFp cells.

TABLE 1

Comparison of virus titers obtained in parallel infections of 1 to 5 × $10^5$ cells in cavities of 24-well plates. Input virus was adjusted for an MOI of 0.1. CEFp, fresh primary chicken embryonic fibroblasts; membrane, extra-embryonic membrane. MVA yield in pfu/ml (after 48 h, infection with MOI of 0.1)

| | |
|---|---|
| CEFp | 3.54 × $10^7$ |
| retina | 2.06 × $10^7$ |
| liver | 3.20 × $10^4$ |
| somite | 4.60 × $10^7$ |
| membrane | 4.03 × $10^3$ |

Plaque-forming units for MVA on duck cells were determined as follows: MVA virus was recovered from infected cells after 48 hours from the supernatant and from adherent cells opened by repeated freeze-thawing. VERO (African green monkey kidney) cells were seeded in 96 well plates (2×$10^4$ cells per well) and infected with serial 10-fold dilutions of MVA-containing suspension on the following day. Two days thereafter, the cultures were fixed with methanol and infected cells incubated with polyclonal vaccinia virus antibodies (Quartett, Germany, #9503-2057, at 1:1000 dilution in PBS containing 1% fetal calf serum) for 1 hour at 37° C. Two wash steps were performed with PBS containing 0.05% Tween 20 (Sigma Corp, USA) and secondary antibody to the vaccinia-specific antibody is added at 1:1000 dilution in PBS containing 1% fetal calf serum. This secondary antibody is coupled to the peroxidase enzyme that catalyzes a color reaction upon incubation with AEC reagent (3-amino-9-ethyl-carbozole; 0.3 mg/ml in 0.1 M acetate buffer pH 5.0 containing 0.015% $H_2O_2$). Infected foci are identified by light microscopy and plaque forming units are calculated from the maximum dilution of MVA suspension that yields a positive dye reaction.

FIG. 5 depicts the output of virus per cell. The output of virus per cell correlates with permissiveness of a given host cell for a particular virus. Permissiveness is influenced by biochemical properties such as receptor density or efficiency of processing of viral structural proteins. FIG. 5 demonstrates that the number of infectious particles released per retina cell or per somite cell compares favourably with the obtained infectious particles per chicken embryonic fibroblast.

Division of "output virus per cell" by the "MOI" yields the burst size, the ratio of input virus to output virus. Burst size is equivialent to amplification of virus and thus important to estimate cost and required resources for large scale production. The determined burst sizes in the described example are 374 for CEFp, 513 for retina cells, and 1108 for somite-derived cells. Retina cells and somite cells yield better values than fresh primary chicken embryo fibroblasts and thus should provide superior substrates for large scale production of MVA.

The unsatisfactory results for MVA amplification obtained with cells derived from liver or extra-embryonic membrane cannot be extended to other virus families: it is evident to one familiar with the art that amplification of other viruses, for example vaccine-relevant influenza viruses; may be extremely successful on these cells.

It is conceivable that with subsequent passaging of virus on a given host cell the output titer decreases. Such events may occur if host cells support most but not all steps in the various stages of the infectious cycle. To address this question serial passage of MVA was performed on duck retina cells transformed with plasmid 49E. The data in FIG. 6 demonstrate that MVA is not lost with passaging on these cells: at similar levels of input virus adjusted to an MOI of 0.3 (given by bars in FIG. 6) the burst size (bold squares) increases nine-fold from 35 to 315. The reason for the increase in burst size may be due to to improved properties of the host cell as passage number increases.

In conclusion, duck retina and somite-derived cells obtained by transfection of Ad5-E1 region under CGMP conditions stably support amplification of MVA with an efficiency comparable to or better than primary chicken embryonic fibroblasts. Due to the highly attenuated nature of MVA conventional cell lines for large-scale production of viruses are not suitable. It is a surprising finding that designed duck cell lines performed better than primary chicken cells in propagation of MVA and thus are able to provide novel production platforms for this important vaccine candidate. The described cell lines were generated under cGMP conditions and are therefore suitable for pharmaceutical application.

The invention claimed is:

1. An immortal duck cell line comprising:

(i) a first viral gene which is a Mastadenovirus early region 1A (E1A) gene wherein said E1A gene has the sequence of bp 1193 to 2309 of SEQ ID NO: 7 or the sequence complementary to bp 4230 to 3113 of SEQ ID NO: 9, wherein the expression of said first gene is driven by a human phosphoglycerate kinase (PGK) promoter; and (ii) a second viral gene which codes for a Mastadenovirus early region 1B 55K (E1B 55K) protein wherein said E1B gene has the sequence of bp 1145 to 3007 of SEQ ID NO: 8 or the sequence complementary to bp 2345 to 550 of SEQ ID NO: 9, wherein the expression of said second gene is driven by a mouse cytomegalovirus (CMV) immediate early promoter or a human herpesvirus thymidine kinase (tk) promoter, and wherein said first and second viral genes are integrated and stably expressed in said duck cell line.

2. The duck cell line of claim 1, wherein the cell line is obtained from duck somites or duck retina.

3. The duck cell line of claim 1, further comprising non-natural functional sequences comprising transgenes, enhancers or selection markers.

4. The duck cell line of claim 1, wherein the cell line is free of reverse transcriptase activity.

5. The duck cell line of claim 1, which is duck cell line 12A07-A10 (DSM ACC2695).

6. A method for preparing the immortal duck cell line of claim 1, comprising transforming or transfecting a duck primary cell with a first gene which is a Mastadenovirus early region 1A (E1A) gene, wherein said E1A gene has the sequence of bp 1193 to 2309 of SEQ ID NO: 7 or the sequence complementary to bp 4230 to 3113 of SEQ ID NO: 9, wherein the expression of said first gene is driven by a human phosphoglycerate kinase (PGK) promoter, and a second gene which codes for a Mastadenovirus early region 1B 55K (E1B 55K) protein, wherein said E1B gene has the sequence of bp 1145 to 3007 of SEQ ID NO: 8 or the sequence complementary to bp 2345 to 550 of SEQ ID NO: 9, and wherein the expression of said second gene is driven by a mouse cytomegalovirus (CMV) immediate early promoter or a human herpesvirus thymidine kinase (tk) promoter.

7. The method of claim 6 comprising non-viral transfection of the duck starting cell.

8. A method for producing viruses or biological recombinant proteins, comprising, a) providing to the cells of the immortal duck cell line of claim 1 a virus, or a gene coding for a recombinant protein operably linked to a promoter;

b) incubating the cells; and c) harvesting the virus progeny or the recombinant proteins from the cells.

9. The method of claim 8 wherein the cells are contacted by a pox virus, or pox virus strain MVA, and wherein the immortal duck cell line originates from duck somites or duck retina.

10. The duck cell line of claim 1, wherein the first gene and the second gene are located on different nucleic acid segments.

11. The duck cell line of claim 1, which is suitable for production of biologicals or viruses including vaccine strains and recombinant viral vectors.

12. The duck cell line of claim 1, wherein a plasmid encoded by SEQ ID NO: 18 is used for immortalization of the duck cell line.

13. The duck cell line of claim 1, wherein a plasmid encoded by SEQ ID NO: 9 is used for immortalization of the duck cell line.

14. The duck cell line of claim 1, wherein the cells subjected to immortalization are selected from primary cells, cells from isolated body segments, and cells from separated individual organs.

15. The duck cell line of claim 14, wherein the isolated body segments are somites.

16. The duck cell line of claim 14, wherein the separated individual organs are selected from retina and extraembryonic tissues and membranes protecting the embryo.

17. The duck cell line of claim 1, wherein the cell line is cultivable in a chemically defined medium, which is free of animal serum.

* * * * *